United States Patent
Miyagawa et al.

(10) Patent No.: US 10,631,930 B1
(45) Date of Patent: Apr. 28, 2020

(54) ABLATION SYSTEM AND ABLATION DEVICE

(71) Applicant: Nipro Corporation, Osaka (JP)

(72) Inventors: Katsuya Miyagawa, Osaka (JP); Yuuki Nishimura, Osaka (JP); Natsumi Shimazaki, Osaka (JP)

(73) Assignee: Nipro Corporation, Osaka (JP)

( * ) Notice: Subject to any disclaimer, the term of this patent is extended or adjusted under 35 U.S.C. 154(b) by 1030 days.

(21) Appl. No.: 15/028,090

(22) PCT Filed: Oct. 14, 2014

(86) PCT No.: PCT/JP2014/077296
§ 371 (c)(1),
(2) Date: Oct. 25, 2016

(87) PCT Pub. No.: WO2015/056662
PCT Pub. Date: Apr. 23, 2015

(30) Foreign Application Priority Data

Oct. 15, 2013 (JP) .................. 2013-214549
Oct. 15, 2013 (JP) .................. 2013-214550
(Continued)

(51) Int. Cl.
*A61B 18/24* (2006.01)
*A61B 18/00* (2006.01)

(52) U.S. Cl.
CPC ...... *A61B 18/24* (2013.01); *A61B 2018/0022* (2013.01); *A61B 2018/00023* (2013.01);
(Continued)

(58) Field of Classification Search
CPC .......... A61B 18/24; A61B 2018/00023; A61B 2018/0022; A61B 2018/00404;
(Continued)

(56) References Cited

U.S. PATENT DOCUMENTS

| 5,454,807 A | 10/1995 | Lennox et al. |
| 5,486,171 A | 1/1996 | Chou |

(Continued)

FOREIGN PATENT DOCUMENTS

| CN | 101400313 A | 4/2009 |
| JP | 63032459 U1 | 9/1989 |

(Continued)

OTHER PUBLICATIONS

European patent application No. 14853946.3, Extended European Search Report, dated Sep. 21, 2017.
(Continued)

*Primary Examiner* — Christopher A Flory
*Assistant Examiner* — Vynn V Huh
(74) *Attorney, Agent, or Firm* — Marshall, Gerstein & Borun LLP

(57) ABSTRACT

[Object] To provide an ablation system capable of suppressing heat damages to the lumen intima.
[Solution] An ablation system 10 has an ablation device 11 in which a balloon 21 is provided on the distal end side of a shaft 22 and an in-side tube 27 causing a fluid to flow into the balloon 21, the internal space of the shaft 22 causing a fluid to flow out of the balloon 21, and an optical fiber 29 guiding laser light into the balloon 21 are individually provided along the shaft 22, a laser light generating unit 12 emitting laser light to the optical fiber 29, and a fluid returning unit 13 returning a fluid into the internal space of the balloon 21. The ablation device 11 has a reflector 33 reflecting laser light emitted from the optical fiber 29 in the balloon 21, in which the reflector 33 is movable along the axial direction 191 in the balloon 21 and is rotatable in the axial direction 101 as the axis line.

7 Claims, 15 Drawing Sheets

(30) Foreign Application Priority Data

May 20, 2014 (JP) .................................. 2014-104452
May 20, 2014 (JP) .................................. 2014-104476

(52) U.S. Cl.
CPC .............. *A61B 2018/00404* (2013.01); *A61B 2018/00434* (2013.01); *A61B 2018/00511* (2013.01); *A61B 2018/00577* (2013.01); *A61B 2018/00744* (2013.01); *A61B 2018/00791* (2013.01)

(58) Field of Classification Search
CPC ........... A61B 2018/00434; A61B 2018/00511; A61B 2018/00577; A61B 2018/00744; A61B 2018/00791
See application file for complete search history.

(56) References Cited

U.S. PATENT DOCUMENTS

| | | | |
|---|---|---|---|
| 8,535,298 B1 | 9/2013 | Neev | |
| 2002/0068963 A1 | 6/2002 | Maki et al. | |
| 2003/0060813 A1* | 3/2003 | Loeb | A61B 18/24 606/17 |
| 2003/0199860 A1 | 10/2003 | Loeb et al. | |
| 2005/0131399 A1 | 6/2005 | Loeb et al. | |
| 2005/0273090 A1 | 12/2005 | Nieman et al. | |
| 2005/0288654 A1 | 12/2005 | Nieman et al. | |
| 2006/0217693 A1 | 9/2006 | Gowda et al. | |
| 2007/0208329 A1* | 9/2007 | Ward | A61B 18/24 606/17 |
| 2008/0195085 A1* | 8/2008 | Loeb | A61B 18/18 606/3 |
| 2010/0185187 A1 | 7/2010 | Yamashita et al. | |
| 2014/0207128 A1 | 7/2014 | Iwase et al. | |
| 2014/0323564 A1 | 10/2014 | Pilz et al. | |
| 2016/0008636 A1* | 1/2016 | Warnking | A61B 8/0841 600/411 |

FOREIGN PATENT DOCUMENTS

| | | |
|---|---|---|
| JP | H06343651 A | 12/1994 |
| JP | H07047081 A | 2/1995 |
| JP | H0795987 A | 4/1995 |
| JP | H11333005 A | 12/1999 |
| JP | 2001-502438 A | 2/2001 |
| JP | 2008501444 A | 1/2008 |
| JP | 2008036153 A | 2/2008 |
| JP | 2008-194084 A | 8/2008 |
| JP | 2009533076 A | 9/2009 |
| WO | WO-98/11462 A1 | 3/1998 |
| WO | WO-2007/103721 A2 | 9/2007 |
| WO | WO-2013/017261 A1 | 2/2013 |
| WO | WO-2013/047261 A1 | 4/2013 |

OTHER PUBLICATIONS

Japanese patent application No. 2013-214549, Notification of Reasons for Refusal (English translation), dated Jan. 31, 2017.
Japanese patent application No. 2014-104452, Notification of Reasons for Refusal, dated Feb. 20, 2018.
Japanese patent application No. 2014-104476, Office Action, dated Oct. 31, 2017.
Japanese patent application No. 2014-104476, Office Action, dated Feb. 20, 2018.

* cited by examiner

[Fig. 1]
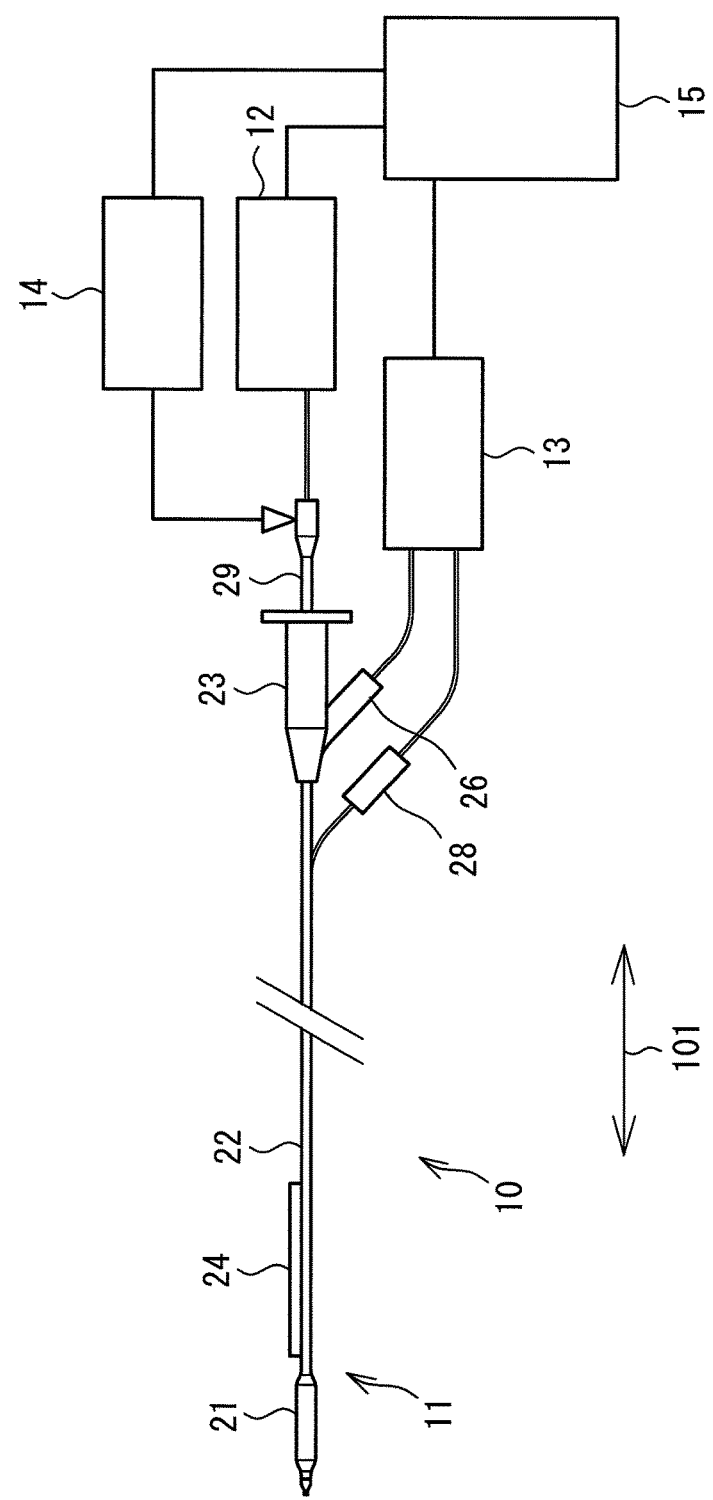

[Fig. 2]
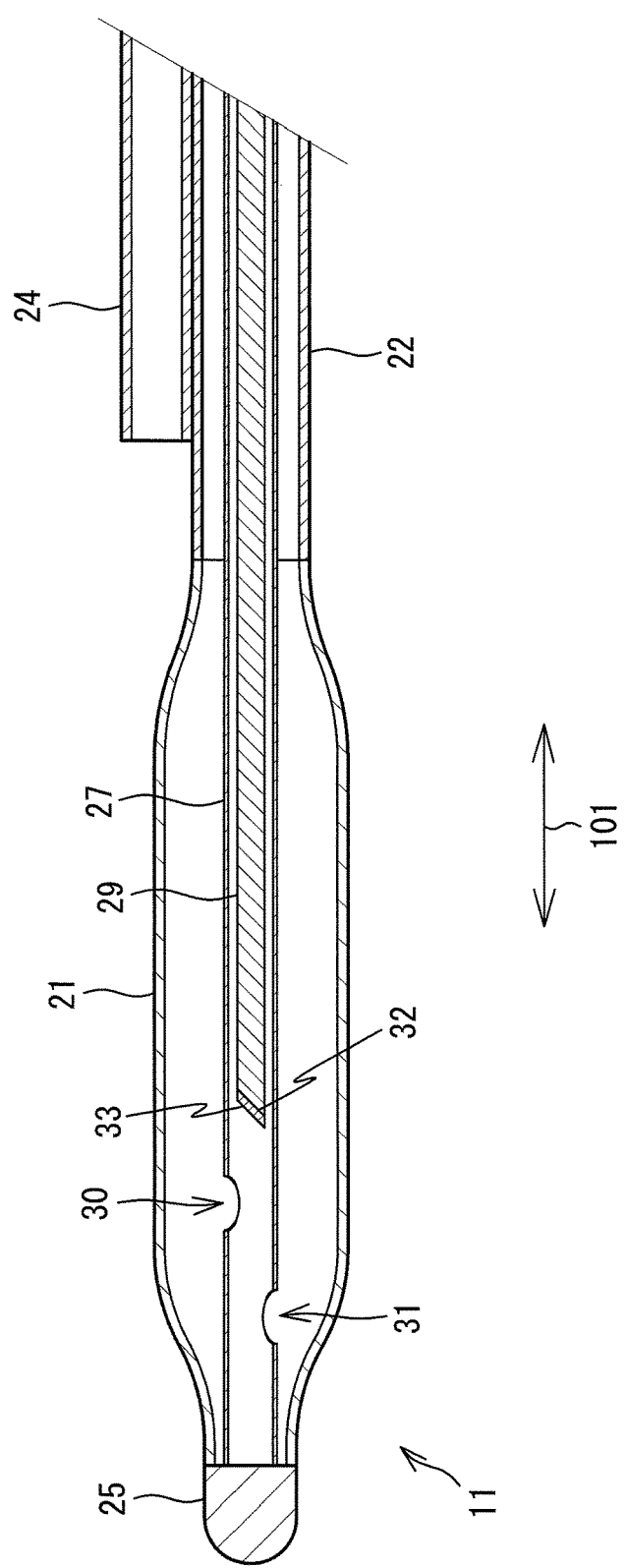

[Fig. 3]
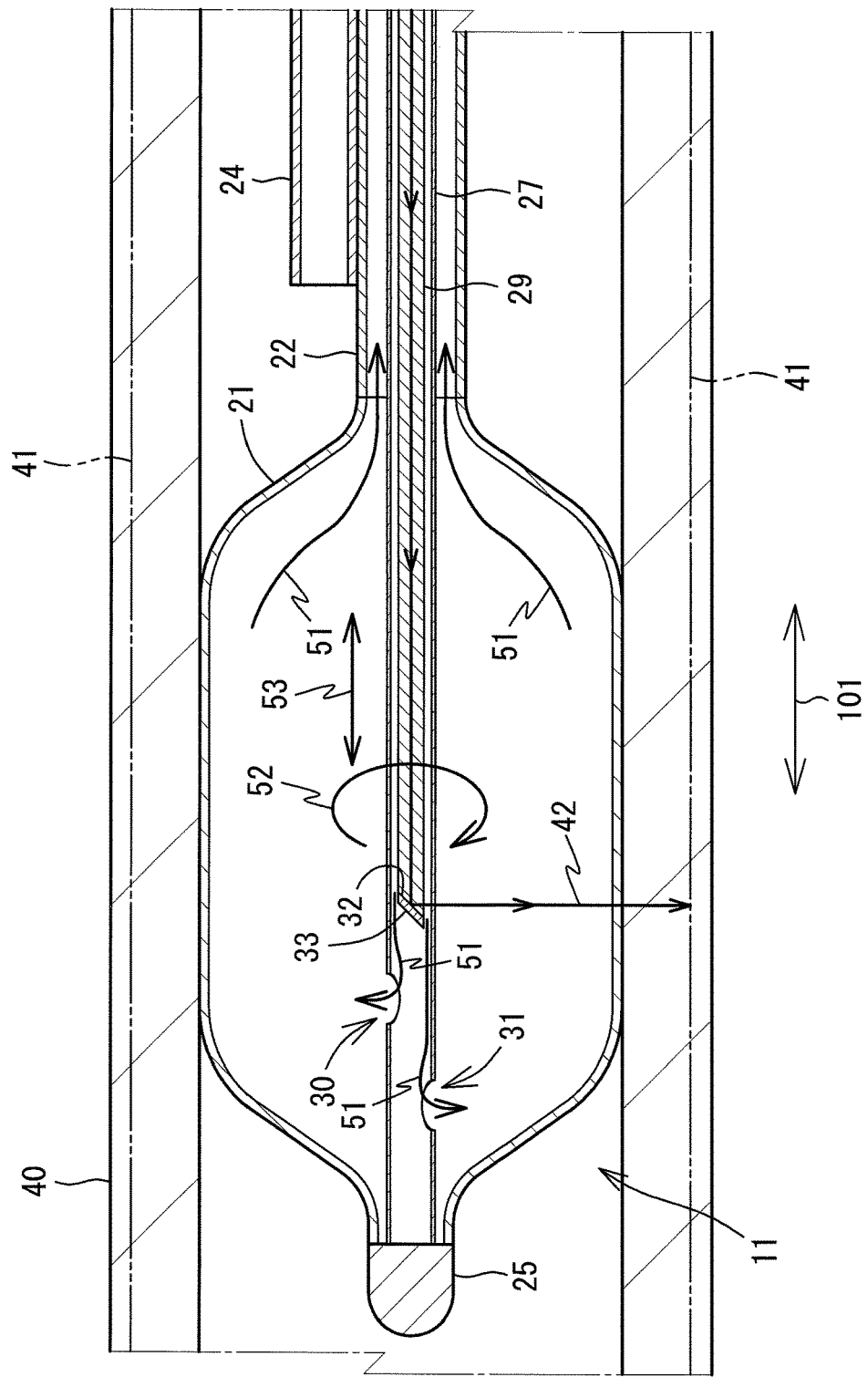

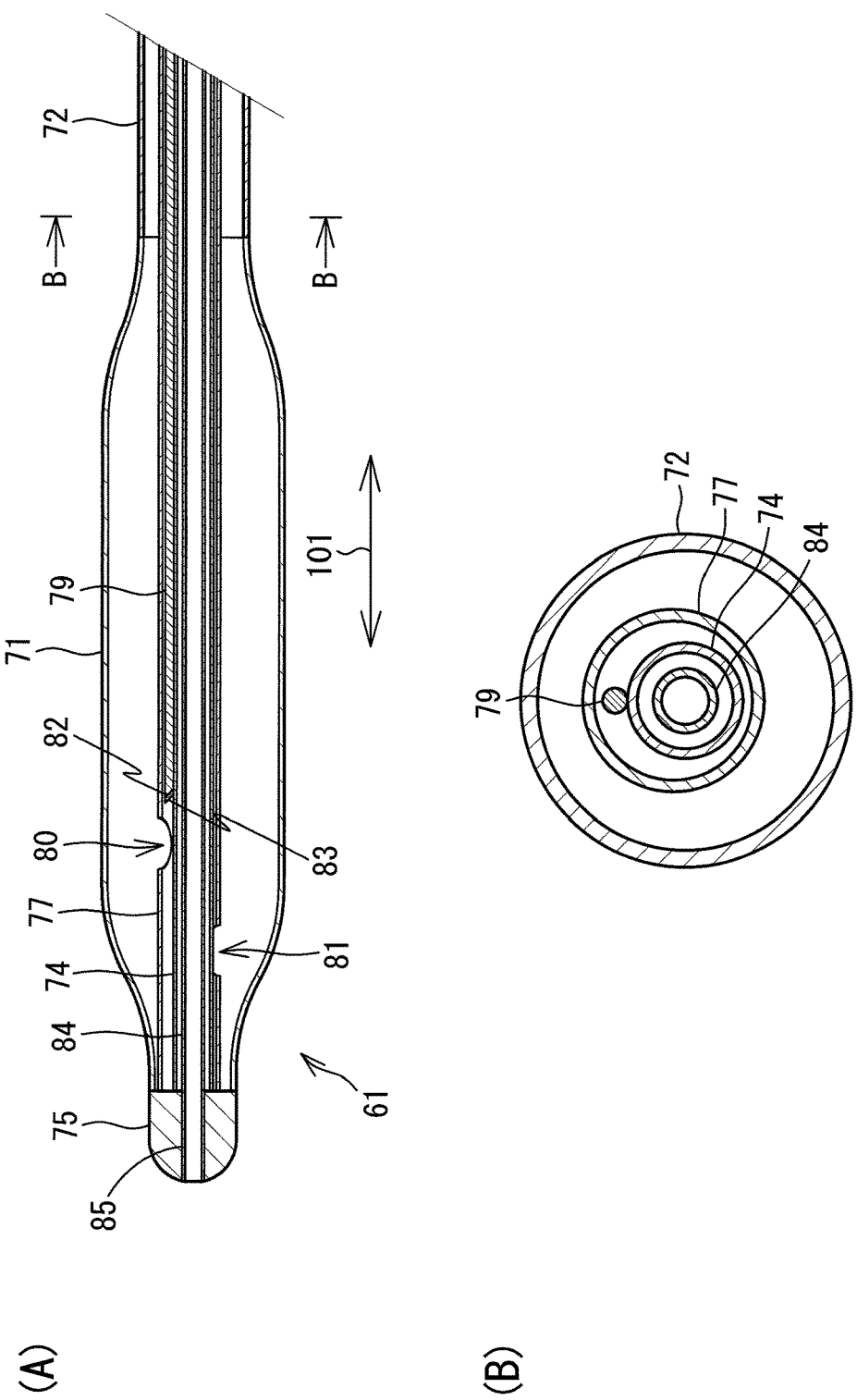
[Fig. 4]

[Fig. 5]
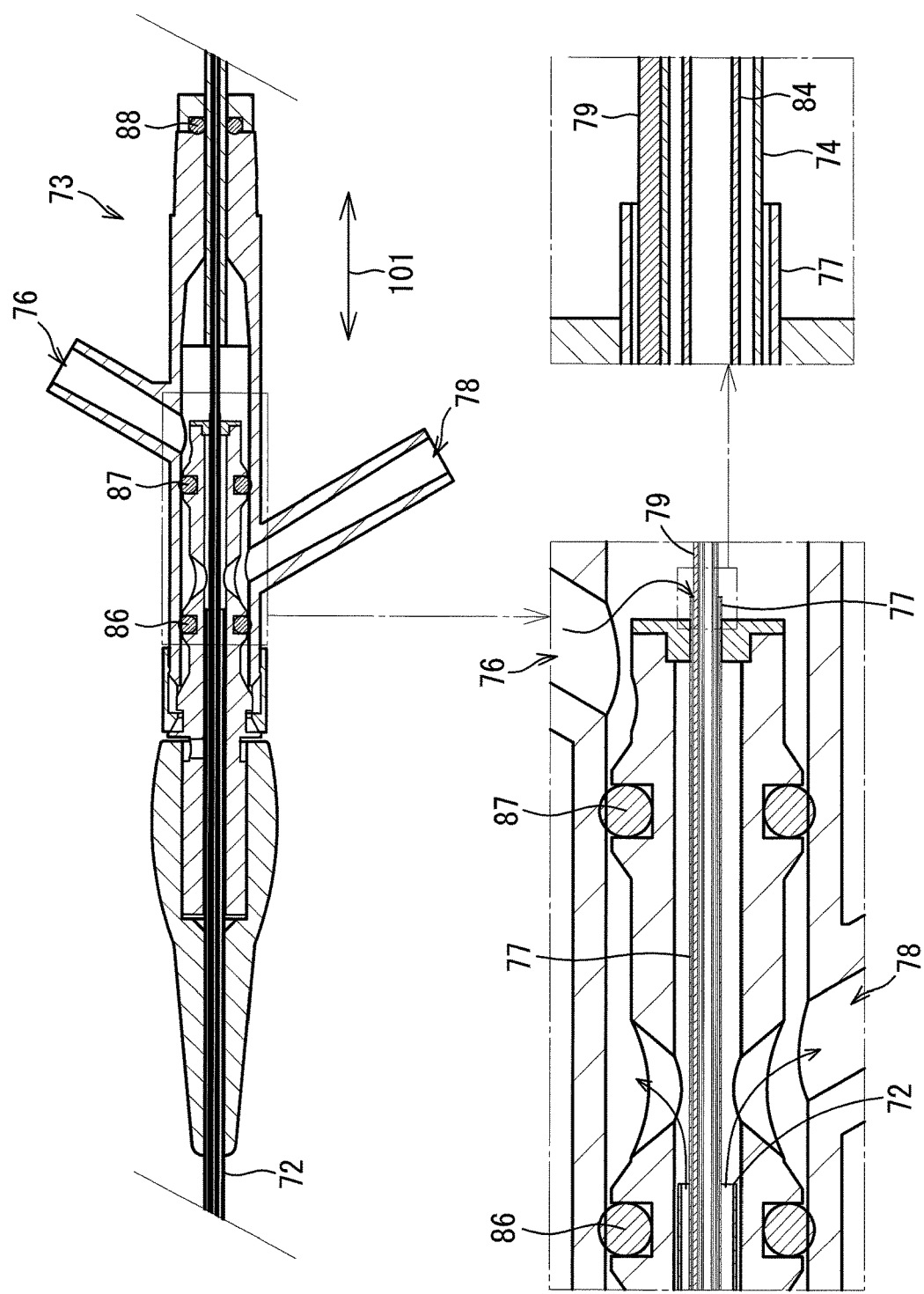

[Fig. 6]
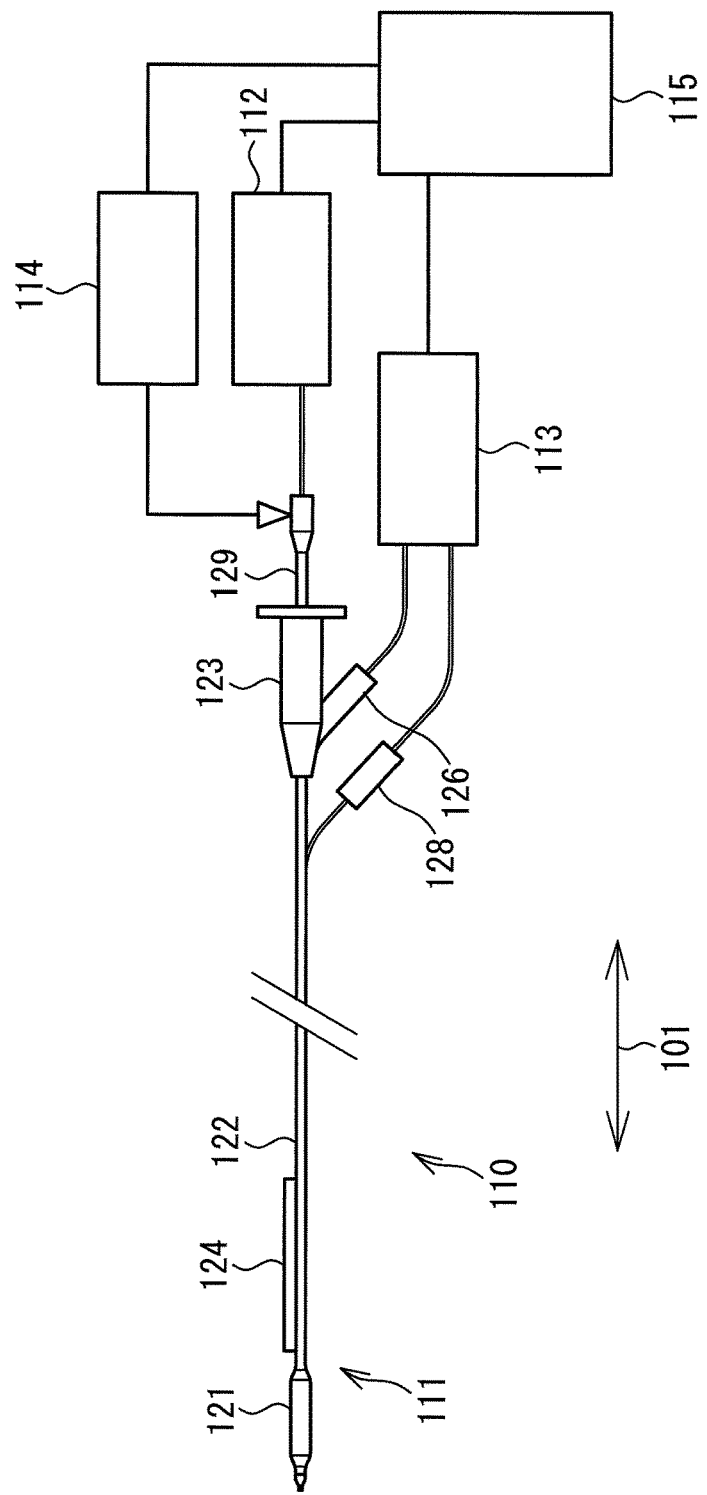

[Fig. 7]
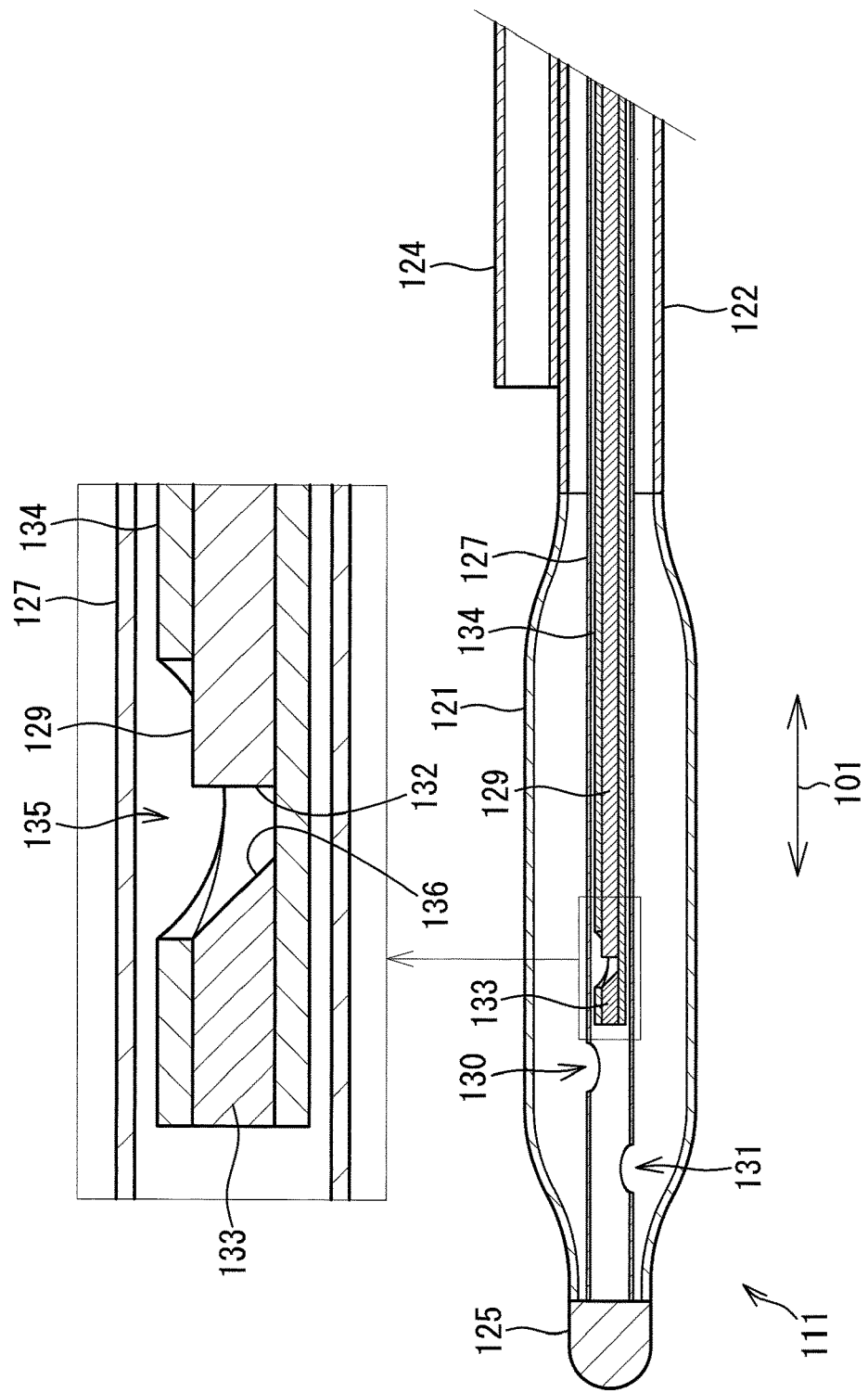

[Fig. 8]
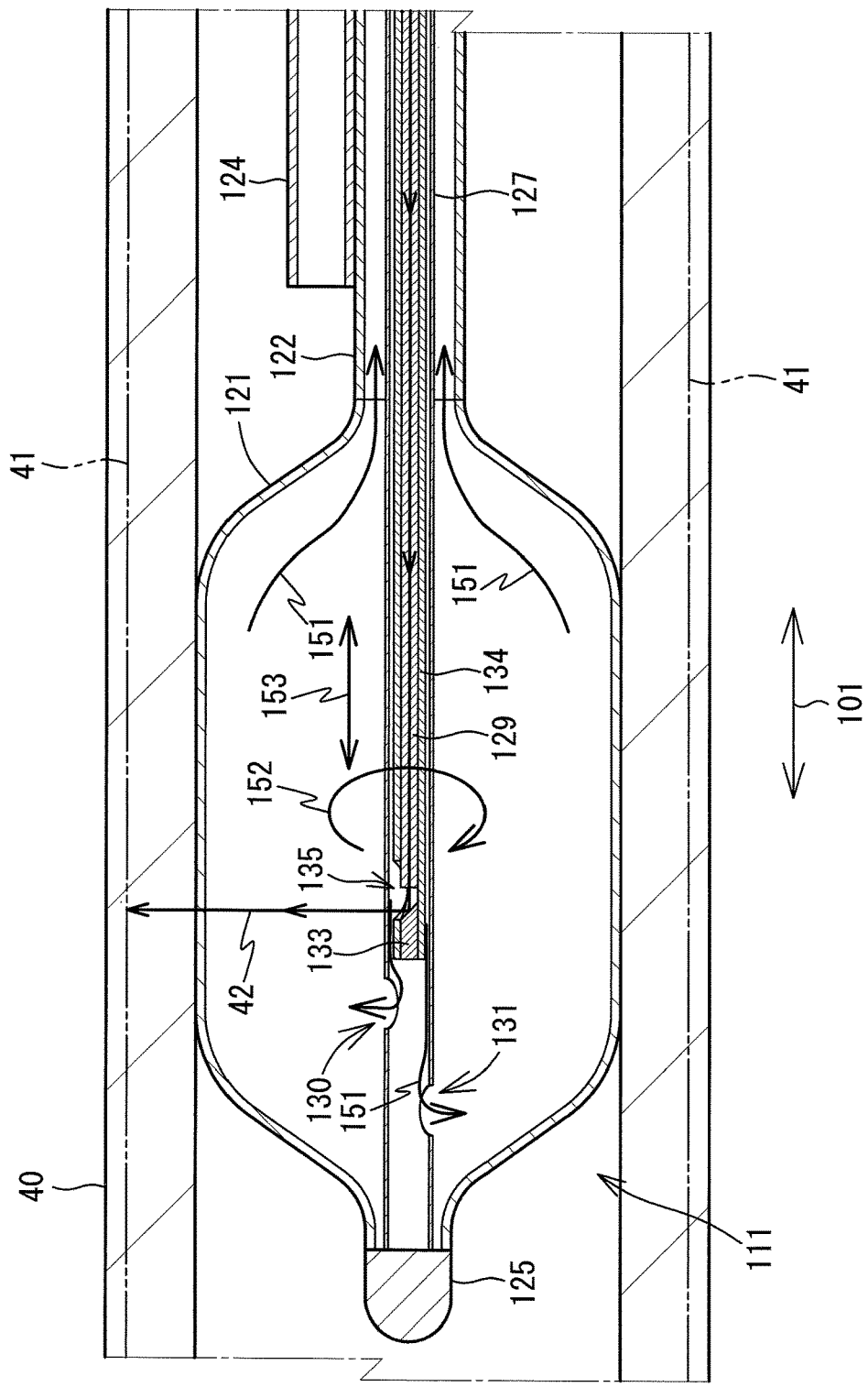

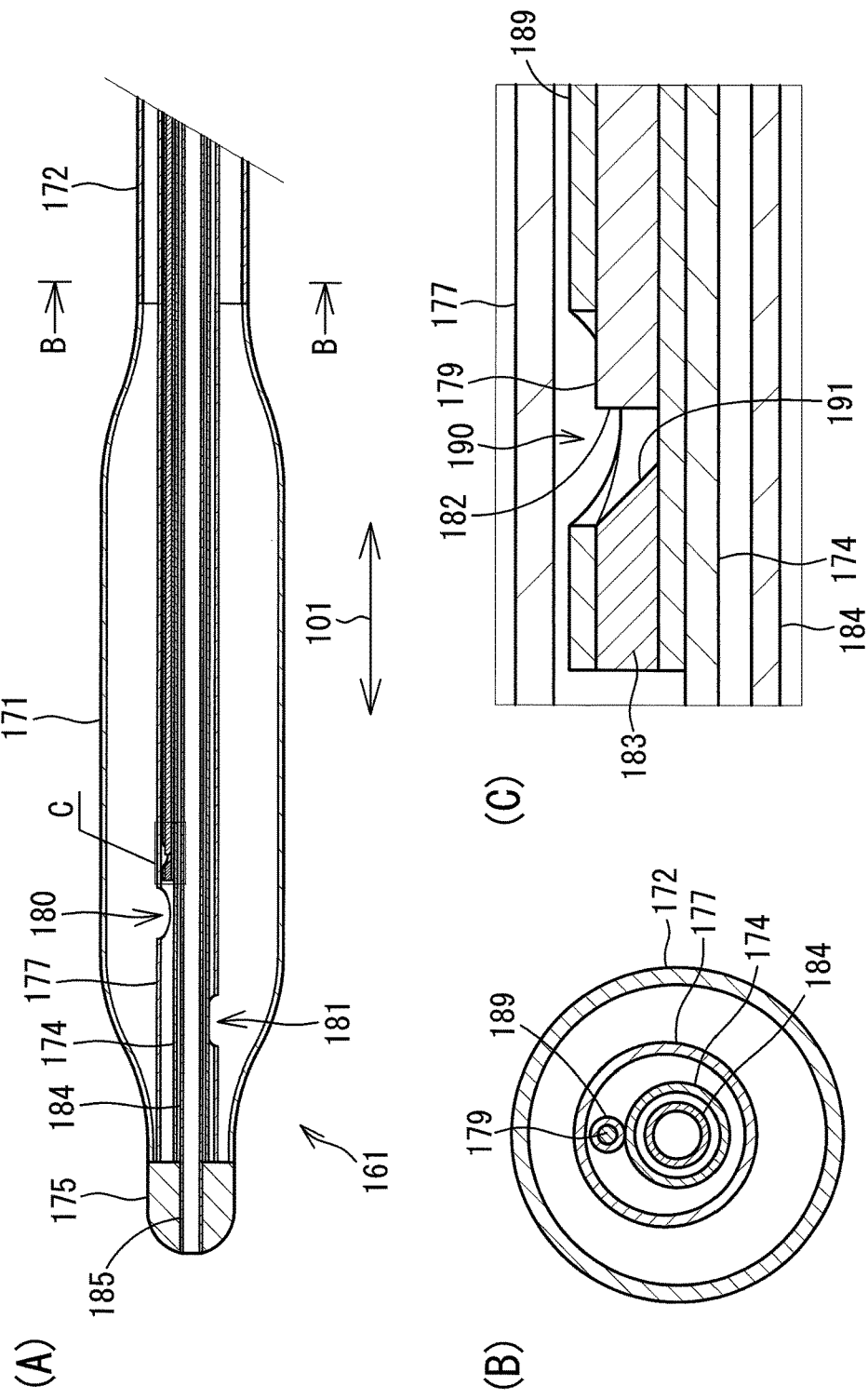
[Fig. 9]

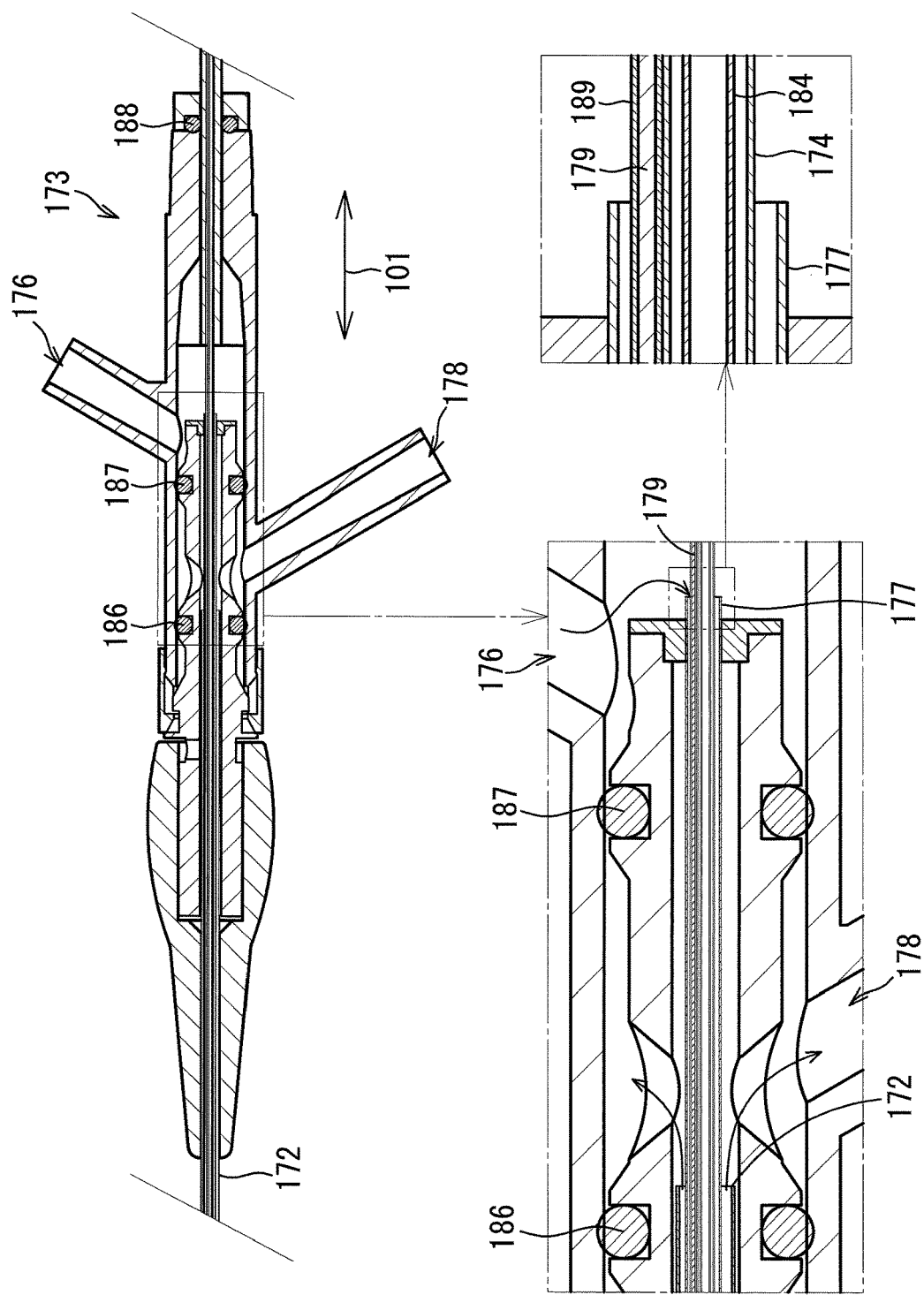
[Fig. 10]

[Fig. 11]
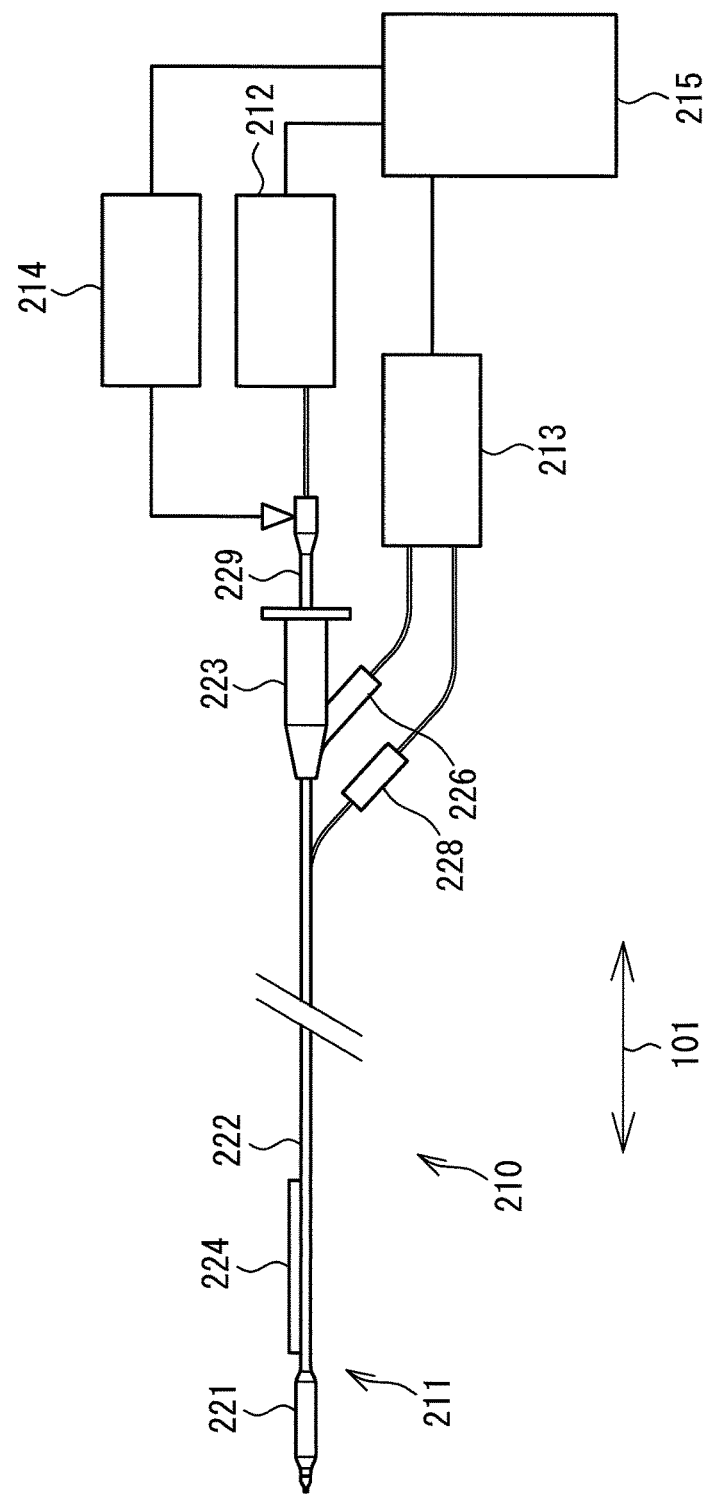

[Fig. 12]
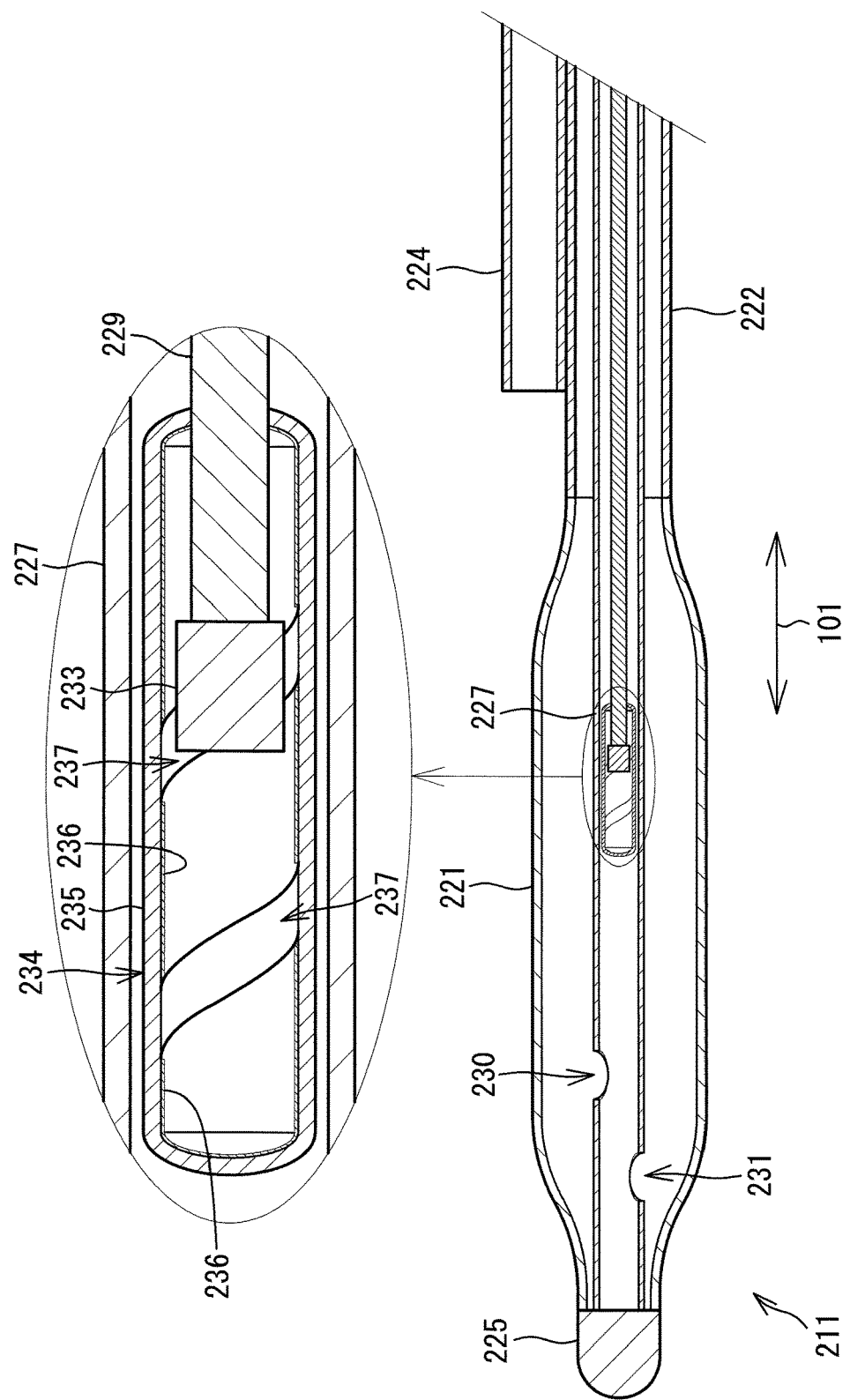

[Fig. 13]
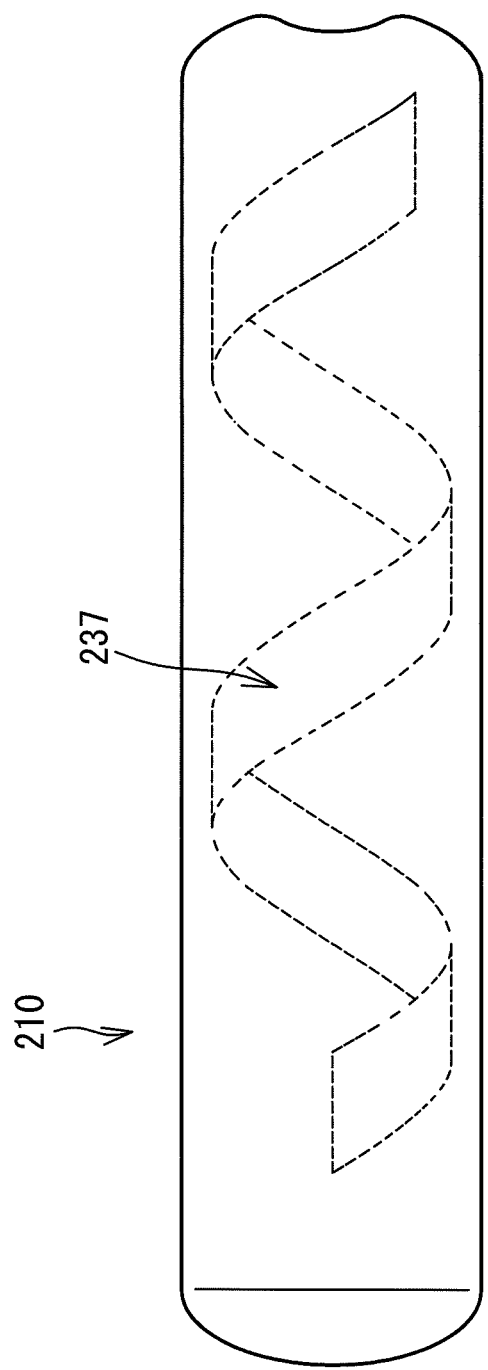

[Fig. 14]
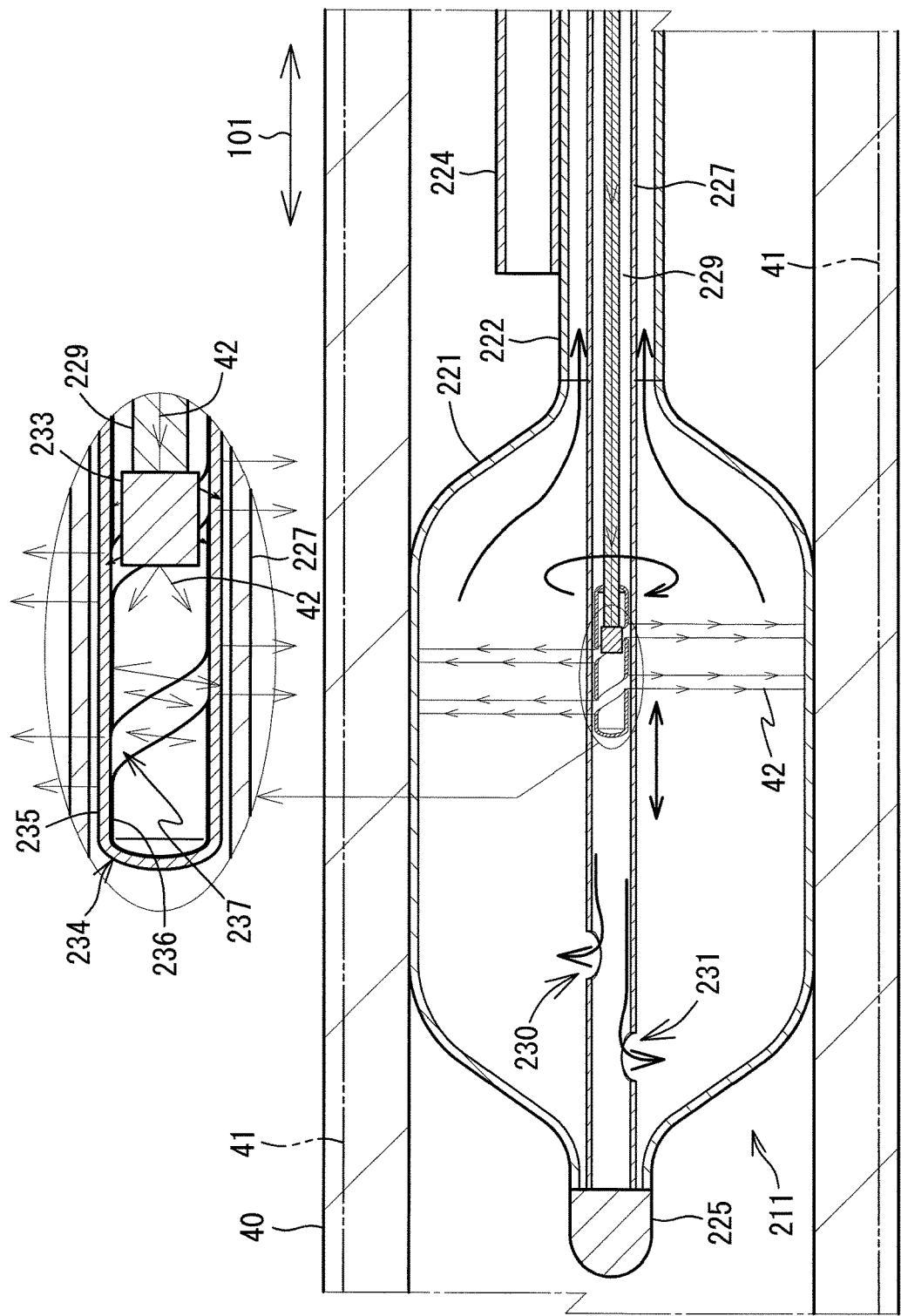

[Fig. 15]
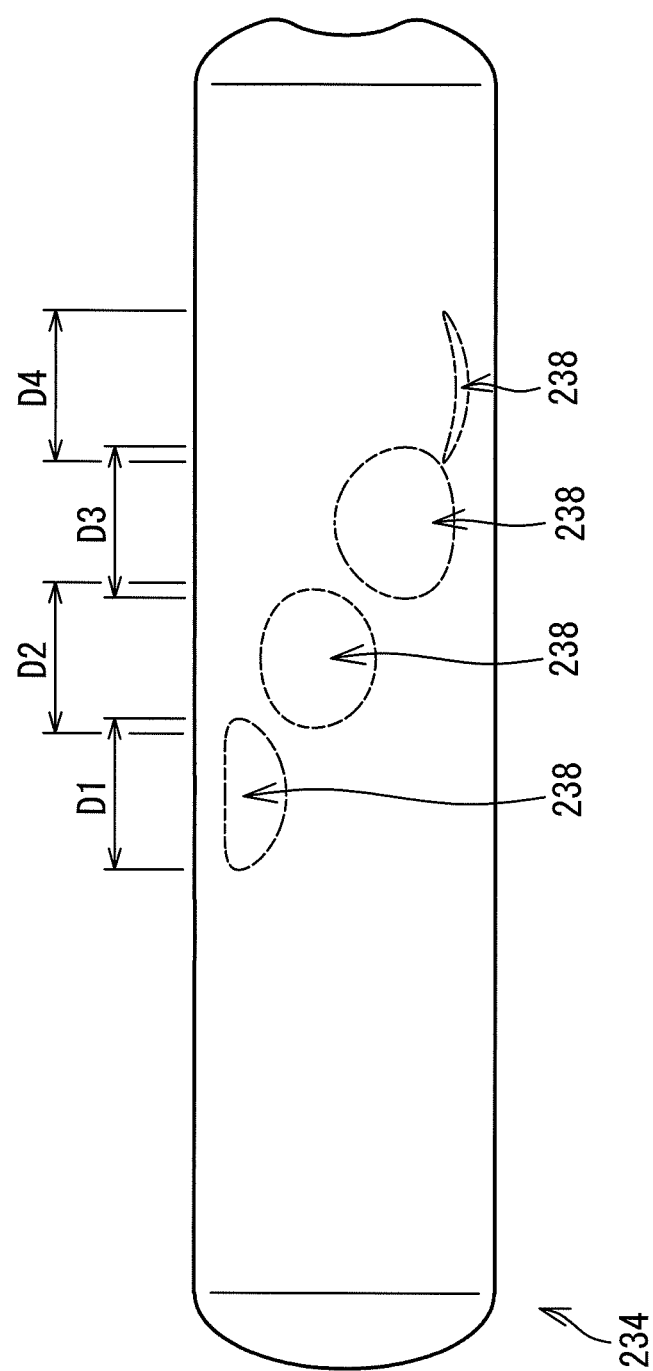

ABLATION SYSTEM AND ABLATION DEVICE

TECHNICAL FIELD

The present invention relates to an ablation system and an ablation device which perform ablation to tissues around the lumen of a living body.

BACKGROUND ART

It is known that, when nerves present in the vicinity of the adventitia of the renal artery are cauterized, the blood pressure decreases over a long period of time. Thus, an application of the knowledge to the treatment of hypertension has been expected. Such a technique of cauterizing the nerves in the renal artery is referred to as renal artery sympathetic nerve ablation or renal denervation. As one renal artery sympathetic nerve ablation, a technique is mentioned which includes inserting a balloon catheter having an electrode into the right and left renal arteries, heating is performed from the intracavity of the renal arteries by generating heat by the electrode, and then transmitting the heat to the adventitia of the renal arteries for cauterizing the nerves.

However, when heat of about 60 to 70° C. required for cauterizing the nerves is transmitted from the intracavity to the adventitia of the renal arteries, there are concerns about problems that adverse effects, such as an edema and a thrombus, arise with high frequency due to the heat given to the intima. Moreover, since it takes several minutes to transmit the necessary heat from the intracavity to the adventitia, heat and pain may be given to a patient during the transmission.

To address the problems described above, a device has been proposed which includes guiding a pulse laser to the renal artery using a catheter, condensing the pulse laser to the adventitia of the renal artery by a condenser lens, and then causing multiphoton absorption at a focal position to perform ablation to the adventitia at the focal position (Patent Literatures 1 and 2).

CITATION LIST

Patent Literature

Patent Literature 1: International publication No. WO2013/017261
Patent Literature 2: International publication No. WO2013/047261

SUMMARY OF INVENTION

Technical Problems

However, the devices described in Patent Literatures 1 and 2 have a problem that, since the condenser lens and the like are disposed in the catheter, the structure of the catheter becomes complicated. Moreover, there is a problem that, since the focal position of the pulsed laser depends on the thickness of the vascular wall or the position of the catheter in blood vessels, it is difficult to position the focal position of the pulsed laser to a desired position with good accuracy. For example, a problem may arise that, since the thickness of the vascular wall varies depending on individuals, the thickness of the vascular wall of an individual to be subjected to ablation is measured beforehand, and then the focal position of the condenser lens needs to be adjusted to the thickness of the vascular wall and a problem may arise that, when the position of the catheter is shifted from the center of a blood vessel, the focal position of the pulsed laser is not uniform with respect to the thickness direction of the vascular wall in the circumferential direction of the blood vessel.

Moreover, in order to perform the ablation with good efficiency in a short period of time, it is desirable to increase the output of the laser light. However, when the output of the laser light is increased, there is a possibility that damages, such as burning and peeling, may arise in a reflector and the like.

The present invention has been made in view of the circumstances described above. It is an object of the present invention to provide an ablation system or an ablation device capable of heating tissues in a depth portion around the lumen of a living body and suppressing heat damages to the lumen intima.

It is another object of the present invention to provide an ablation device which is difficult to cause damages in a reflector even when the output of laser light is increased.

Solution to the Problems (1) An ablation system according to the present invention has an ablation device provided with a balloon which is elastically expandable on the distal end side of a shaft and having a first lumen causing a fluid to flow into the balloon, a second lumen causing a fluid to flow out of the balloon, and a light guide material guiding laser light into the balloon which are individually provided along the shaft, a laser light generating unit emitting laser light to the light guide material, and a fluid returning unit returning a fluid into the internal space of the balloon through the first lumen and the second lumen. The ablation device has a reflector which reflects laser light emitted from the light guide material in a second direction crossing a first direction in which the light guide material is extended in the balloon and at least the reflector is movable along the first direction in the balloon and is rotatable in the first direction as the axis line.

In the ablation device inserted into the lumen of a living body, the balloon is expanded at a desired position, and then the fluid returning unit causes a fluid to return into the internal space of the balloon through the first lumen and the second lumen. The laser light emitted from the laser light generating unit is guided into the balloon by the light guide material to be reflected in the second direction by the reflector. Thus, the laser light is emitted to a tissue around the lumen of a living body. Due to the fact that the reflector is rotated in the first direction as the axis line while being moved along the first direction in the balloon, the laser light is uniformly emitted to the tissue around the lumen of a living body. Since the balloon contacts the inner surface of the lumen, the heating to the inner surface by the laser light is suppressed by being cooled by the fluid returning into the balloon.

(2) The reflector is integrally provided on the distal end side of the light guide material and the light guide material is movable along the first direction and is rotatable in the first direction as the axis line with respect to the shaft.

Thus, the ablation device can be realized with a simple configuration. By operating the light guide material on the proximal end side of the shaft, the reflector is rotated in the first direction as the axis line while being moved along the first direction in the balloon.

(3) The laser light generating unit may emit laser light having a continuously and periodically changing waveform to the light guide material.

(4) The present invention may be construed as an ablation device having a shaft, a balloon which is provided on the distal end side of the shaft and which is elastically expandable, a first lumen provided along the shaft and causing a fluid to flow into the balloon, a second lumen provided along the shaft and causing a fluid to flow out of the balloon, a light guide material provided along the shaft and guiding laser light into the balloon, and a reflector reflecting laser light emitted from the light guide material in a second direction crossing a first direction in which the light guide material is extended in the balloon, in which at least the reflector is movable along the first direction in the balloon and is rotatable in the first direction as the axis line.

(5) The reflector may be integrally provided on the distal end side of the light guide material and the light guide material may be movable along the first direction and may be rotatable in the first direction as the axis line with respect to the shaft.

(6) The ablation device according to the present invention has a main shaft having a fluid lumen through which a fluid passes, a balloon which is provided on the distal end side of the main shaft and which is expandable by the fluid passing through the fluid lumen, a sub-shaft which has a wire lumen, which allows insertion and passing of a guide wire, and which is inserted into and passed through the inside of the main shaft to be extended into the balloon, a light guide material which is provided along the sub-shaft and which guides laser light into the balloon, and a reflector which reflects laser light emitted from the light guide material in a direction crossing the axial direction in the balloon. The sub-shaft is movable in the axial direction and is rotatable around the axial direction with respect to the main shaft. The light guide material and the reflector are movable and rotatable with the sub-shaft.

A guide wire inserted into the lumen of a living body is inserted into and passed through the wire lumen of the ablation device, and then the main shaft is inserted into a desired position of the lumen of a living body along the guide wire. At a desired position, the fluid flows into the balloon, so that the balloon is expanded. The fluid to be caused to flow into the balloon is returned as appropriate. The laser light emitted to the light guide material is guided into the balloon, and then reflected in a direction crossing the axial direction by the reflector. Thus, the laser light is emitted to the tissue around the lumen of a living body. Due to the fact that the sub-shaft is rotated around the axial direction while being moved along the axial direction in the balloon, the light guide material and the reflector are moved and rotated along the outer periphery of the sub-shaft, so that the laser light is uniformly emitted to the tissue around the lumen of a living body. In this case, even when the guide wire is inserted into and passed through the wire lumen of the sub-shaft, the laser light is not blocked by the guide wire. Since the balloon contacts the inner surface of the lumen, the heating to the inner surface by the laser light is cooled by the fluid returning into the balloon.

(7) The reflector may be integrally provided on the distal end side of the light guide material.

Thus, the ablation device can be realized with a simple configuration.

(8) The sub-shaft may be inserted into and passed through the fluid lumen.

Thus, the reflector is cooled by the fluid which is caused to pass through the fluid lumen.

(9) A connector having a port through which a fluid passes is connected to the proximal end side of the main shaft. The port is connected to the fluid lumen in such a manner that a fluid can pass. The sub-shaft and the light guide material are rotatable around the axial direction with respect to the connector.

Thus, the operation of the sub-shaft, the light guide material, and the reflector is facilitated on the connector side.

(10) The present invention may be construed as an ablation system having the ablation device described above, a laser light generating unit emitting laser light to the light guide material, and a fluid returning unit returning a fluid into the internal space of the balloon through the fluid lumen.

(11) An ablation device according to the present invention has a shaft, a balloon which is provided on the distal end side of the shaft and which is elastically expandable, a fluid lumen provided along the shaft and causes a fluid to pass into the balloon, a light guide material provided along the shaft and guiding laser light into the balloon, and a reflector reflecting laser light emitted from the light guide material in a second direction crossing a first direction in which the light guide material is extended in the balloon. The reflector is disposed facing the distal end of the light guide material in the first direction.

In the ablation device inserted into the lumen of a living body, a fluid is caused to pass, so that the balloon is expanded at a desired position. The laser light is guided by the light guide material into the balloon, and then reflected in the second direction by the reflector. Thus, the laser light is emitted to the tissue around the lumen of a living body. Since the balloon contacts the inner surface of the lumen of a living body, the heating to the inner surface by the laser light is suppressed by being cooled by the fluid in the balloon. Since the reflector is disposed facing the distal end of the light guide material, the reflector is difficult to be damaged by the laser light.

(12) Preferably, the reflector is disposed in a flow passage of the fluid passing into the balloon.

Thus, the reflector is cooled by the fluid, and therefore damages caused by the laser light are further suppressed.

(13) Preferably, the reflector has a metal layer on the surface.

(14) Preferably, the reflector is movable along the first direction in the balloon and is rotatable around the axis line of the shaft along the first direction.

Due to the fact that the reflector is rotated around the axis line of the shaft while being moved along the first direction in the balloon, the laser light is uniformly emitted to the tissue around the lumen of a living body. The rotation of the reflector around the axis line of the shaft includes the rotation of the reflector at a position spaced from the axis line of the shaft and the rotation of the reflector on the axis line of the shaft.

(15) Preferably, a light guide tube which is movable along the first direction in the balloon and is rotatable around the axis line of the shaft along the first direction is provided along the shaft and the light guide material and the reflector are disposed in the internal space of the light guide tube.

Thus, the light guide material and the reflector are movable and rotatable in the state where the light guide material and the reflector maintain the mutual positional relationship.

(16) Preferably, the light guide tube has an opening which allows an external fluid to contact the reflective surface of the reflector.

Thus, the reflective surface of the reflector is cooled by the fluid.

(17) The present invention may be construed as an ablation system having the ablation device described above, a laser light generating unit emitting laser light to the light guide material, and a fluid returning unit returning a fluid into the internal space of the balloon through the fluid lumen.

(18) The ablation device according to the present invention has a shaft, a balloon which is provided on the distal end side of the shaft and which is elastically expandable, a first lumen which is formed along the shaft and causes a fluid to flow into the balloon, a second lumen which is formed along the shaft and causes a fluid to flow out of the balloon, a light guide material which is provided along the shaft and guides laser light into the balloon, a diffusion member which reflects or diffuses laser light emitted from the light guide material in a direction crossing a first direction in which the light guide material is extended in the balloon, and a tubular member which is provided in the balloon and surrounds the diffusion member and which has a reflective layer reflecting or blocking laser light reflected or diffused by the diffusion member on the inner surface side and has a transmission window which allows transmission of the laser light to the outside of the reflective layer.

In the ablation device inserted into the lumen of a living body, the balloon is expanded at a desired position and a fluid is returned into the internal space of the balloon through the first lumen and the second lumen. The laser light emitted to the light guide material is guided into the balloon, and then reflected or diffused by the diffusion member in the direction crossing the first direction. The reflected or diffused laser light is reflected by the reflective layer of the tubular member. On the other hand, the reflected or diffused laser light travels toward the outside of the tubular member, i.e., the tissue around the lumen of a living body from the transmission window of the tubular member. Since the balloon contacts the inner surface of the lumen of a living body, the heating to the inner surface by the laser light is suppressed by being cooled by the fluid returning into the balloon.

(19) The tubular member may be movable in a direction in which at least either a position in the circumferential direction in which the first direction is the axis line or a position in the first direction of the transmission window is displaced.

Since the position of the transmission window is displaced by the movement of the tubular member, laser light is uniformly emitted to the tissue around the lumen of a living body.

(20) The diffusion member and the tubular member may be integrally provided with the light guide material.

By the operation of the proximal end side of the light guide material, the movement of the tubular member can be controlled.

(21) The transmission window may have a spiral shape extending in the first direction.

Thus, laser light is uniformly emitted to the tissue around the lumen of a living body.

(22) Two or more of the transmission windows may be provided at positions different in the first direction.

Thus, laser light is uniformly emitted to the tissue around the lumen of a living body.

(23) The two or more of the transmission windows may be disposed at positions different in the circumferential direction in which the first direction is the axis line.

In the first direction, the direction of laser light travelling in the circumferential direction varies, and therefore the laser light is not concentrated on a specific position in the first direction. Thus, the heating to the inner surface of the lumen of a living body can be suppressed.

(24) In the two or more of the transmission windows, the transmission ranges may be partially overlapped in the first direction.

Thus, a portion to which laser light is not emitted does not arise in the first direction of the lumen of a living body.

Advantageous Effects of Invention

According to the present invention, while a tissue in a deep portion around the lumen of a living body is being heated, heat damages to the lumen intima can be suppressed.

Moreover, damages to a reflector caused by laser light can be suppressed.

BRIEF DESCRIPTION OF DRAWINGS

FIG. 1 is a view illustrating the configuration of an ablation system 10 having an ablation device 11 in the state where a balloon 21 is in a contraction posture according to a first embodiment.

FIG. 2 illustrates a partial cross section of the ablation device 11.

FIG. 3 is a cross sectional view illustrating the ablation device 11 in the state where ablation is performed to a renal artery 40.

FIG. 4 is a partial cross sectional view in the vicinity of a balloon 71 of an ablation device 61 according to a second embodiment.

FIG. 5 is a partial cross sectional view in the vicinity of a connector portion 73 of the ablation device 61.

FIG. 6 is a view illustrating the configuration of an ablation system 110 having an ablation device 111 in the state where a balloon 121 is in a contraction posture according to a third embodiment.

FIG. 7 illustrates a partial cross section of the ablation device 111.

FIG. 8 is a cross sectional view illustrating the ablation device 111 in the state where ablation is performed to the renal artery 40.

FIG. 9(A) is a partial cross sectional view in the vicinity of a balloon 171 of an ablation device 161 according to a fourth embodiment, FIG. 9(B) is a cross sectional view illustrating the cut surface along the B-B line in FIG. 9(A), and FIG. 9(C) is an enlarged cross sectional view illustrating a portion in the vicinity of a C portion in FIG. 9(A).

FIG. 10 is a partial cross sectional view in the vicinity of a connector portion 173 of the ablation device 161.

FIG. 11 is a view illustrating the configuration of an ablation system 210 having an ablation device 211 in the state where a balloon 221 is in a contraction posture according to a fifth embodiment.

FIG. 12 illustrates a partial cross section of the ablation device 211.

FIG. 13 is a side view of a tubular member 234.

FIG. 14 is a cross sectional view illustrating the ablation device 211 in the state where ablation is performed to the renal artery 40.

FIG. 15 is a side view of a tubular member 234 according to a modification of the fifth embodiment.

DESCRIPTION OF EMBODIMENTS

Hereinafter, preferable embodiments of the present invention are described. It is a matter of course that each embodiment is merely one aspect of the present invention and can be altered insofar as the gist of the present invention is not altered.

First Embodiment

[Ablation System 10]

As illustrated in FIG. 1, an ablation system 10 has an ablation device 11, a laser light generating unit 12, a fluid returning unit 13, a drive mechanism 14, and a control unit 15.

[Ablation Device 11]

As illustrated in FIGS. 1 and 2, the ablation device 11 has a shaft 22 provided with a balloon 21 on the distal end side thereof. The shaft 22 is a long member in an axial direction 101. The shaft 22 is a tubular body which may elastically bend in such a manner as to curve in the axial direction 101. A direction in which the shaft 22 in the state where the shaft 22 does not curve extends is referred to as the axial direction 101 in this specification. The axial direction 101 is equivalent to the first direction.

An in-side tube 27 and an optical fiber 29 are inserted into and passed through the shaft 22. Although the outer diameter and the inner diameter of the shaft 22 do not necessarily need to be fixed in the axial direction 101, it is preferable that the rigidity on the proximal end side is higher than that on the distal end side from the viewpoint of operability. For the shaft 22, known materials for use in a balloon catheter, such as synthetic resin and stainless steel, can be used. The shaft 22 does not necessarily need to be configured from only one material and may be configured by attaching a plurality of parts containing other materials.

In this embodiment, the proximal end refers to the backside (right side in FIG. 1) in a direction in which the ablation device 11 is inserted into a blood vessel. The distal end refers to the front side (left side in FIG. 1) in the direction in which the ablation device 11 is inserted into a blood vessel.

On the distal end side of the shaft 22, the balloon 21 is provided. The balloon 21 elastically expands due to the fact that a fluid (liquid, gas) is caused to flow into the internal space and contracts due to the fact that a fluid is caused to flow out of the internal space. FIGS. 1 and 2 illustrate the balloon 21 in a contraction state. The internal space of the balloon 21 is allowed to communicate with each of the internal space of the shaft 22 and the internal space of the in-side tube 27. When a fluid is caused to flow into the internal space of the balloon 21 through the in-side tube 27, the balloon 21 expands in the radial direction orthogonal to the axial direction 101 in such a manner that the diameter at the center in the axial direction 101 reaches the maximum diameter. Due to the fact that, while a fluid having a flow amount which allows holding of the pressure of the fluid maintaining the expansion of the balloon 21 is being caused to flow into the balloon 21, the fluid is caused to flow out of the balloon 21 through the internal space of the shaft 22, the fluid is returned into the balloon 21. As the materials of the balloon 21 and a method for fixing the balloon 21 and the shaft 22, known materials and methods for use in a balloon catheter can be used. The internal space of the in-side tube 27 is equivalent to the first lumen. The internal space of the shaft 22 is equivalent to the second lumen.

On the proximal end side of the shaft 22, an out port 28 is provided. The out port 28 is continuous with the internal space of the shaft 22. The fluid to be returned into the balloon 21 flows out of the out port 28 through the internal space of the shaft 22.

On the proximal end of the shaft 22, a hub 23 is provided. The optical fiber 29 is inserted into and passed through the hub 23. The hub 23 is provided with an in port 26 separately from an insertion and passing port of the optical fiber 29. The in port 26 is continuous with the internal space of the in-side tube 27. The fluid to be returned into the balloon 21 flows in from the in port 26 through the internal space of the in-side tube 27.

On the outside of the shaft 22, a guide wire tube 24 is provided. The guide wire tube 24 is sufficiently shorter than the length in the axial direction 101 of the shaft 22. The guide wire tube 24 does not necessarily need to be provided on the outside of the shaft 22. For example, the guide wire tube 24 may be inserted into and passed through the internal space of the shaft 22 when a monorail type is adopted instead of a rapid exchange type as in this embodiment.

With respect to the in-side tube 27 inserted into and passed through the inside of the shaft 22, the distal end side reaches the internal space of the balloon 21 and the proximal end side is connected to the in port 26. The distal end side of the in-side tube 27 is connected to a distal tip 25 provided on the distal end side of the balloon 21. In the vicinity of the distal tip 25 of the in-side tube 27, openings 30 and 31 penetrating the peripheral wall of the in-side tube 27 are provided. Through the openings 30 and 31, a fluid passing through the internal space of the in-side tube 27 flows out into the balloon 21. The openings 30 and 31 are disposed at positions different in the circumferential direction with respect to the axial direction 101.

The distal tip 25 is provided with a marker containing a contrast medium as the raw material. Examples of the contrast medium include barium sulfate, bismuth oxide, and bismuth subcarbonate, for example.

The optical fiber 29 is inserted into and passed through the inside of the in-side tube 27 from the hub 23 to be extended into the balloon 21. The optical fiber 29 propagates laser light, which is generated by the laser light generating unit 12 and is emitted to the proximal end of the optical fiber 29, to the distal end. For the optical fiber 29, those having a refractive index which allows total reflection in the wavelength of the laser light are adopted as appropriate. Specifically, a single mode fiber, a polarization maintaining fiber, a multimode fiber, and a bundle fiber for image transmission are mentioned. The optical fiber 29 is equivalent to the light guide material.

A distal end surface 32 of the optical fiber 29 is a plane inclined in such a manner as to form an angle of 45° with respect to the axial direction 101. On the distal end surface 32, a reflector 33 is laminated. For the reflector 33, raw materials which totally reflect the laser light propagating through the optical fiber 29 are adopted. As the materials of the reflector 33, a quartz-based glass and the like are adopted but the materials are not particularly limited.

The optical fiber 29 and the reflector 33 are rotatable around the axial direction 101 integrally with the in-side tube 27 and are slidable in the axial direction 101. The rotation and the slide of the optical fiber 29 and the reflector 33 are controlled by directly or indirectly operating the proximal end side of the optical fiber 29 extended from the hub 23.

Specifically, the optical fiber 29 is rotated and slid by a driving force given from the drive mechanism 14 to the proximal end side of the optical fiber 29.

Although not illustrated in each view, a temperature sensor may be provided on the outer wall or the like of the in-side tube 27 in the balloon 21. As the temperature sensor, known temperature sensors, such as a thermocouple, can be used, for example, insofar as the temperature sensors can be placed in the balloon 21. The temperature of the fluid in the balloon 21 can be monitored by guiding a cable extended from the temperature sensor to the outside. Moreover, a third lumen may be provided in the shaft 22 and imaging members, such as an endoscope, IVUS, and OCT, may be inserted.

For the laser light generating unit 12, known laser light generating devices can be used. In the laser light generating unit 12, light of an excitation source is given to a laser medium, and then oscillation is caused by the reflection of an optical resonator, so that laser light is output, for example. The laser light output from the laser light generating unit 12 is preferably a continuous wave and the wavelength of the laser light is preferably in the range of 400 to 2000 nm. In particular, when the wavelength of the laser light is in the range of 800 to 1500 nm (915 nm, 980 nm, 1470 nm), a local temperature increase can be confirmed, and thus the intima of a renal artery can be appropriately warmed. The laser light generating unit 12 is connected to the proximal end of the optical fiber 29. The laser light output from the laser light generating unit 12 is emitted to the proximal end surface of the optical fiber 29.

For the fluid returning unit 13, known devices having a roller pump and a syringe pump can be used. The fluid returning unit 13 is connected to the in port 26 and the out port 28 of the ablation device 11 through a flow passage, such as a tube. The fluid returning unit 13 has a tank storing a fluid and supplies a fluid to the in port 26 at a desired flow amount and pressure from the tank by a driving force of a pump. The fluid flowing out of the out port 28 may be returned into the tank or may be discarded as a waste fluid. Moreover, the fluid returning unit 13 may have a cooling device for cooling the fluid in the tank. The fluid is not particularly limited and is preferably a mixed solution of physiological saline and a contrast medium for the purpose of the ablation of a renal artery.

The drive mechanism 14 gives a driving force which rotates and slides the proximal end side of the optical fiber 29 in the axial direction 101, and a mechanism in which a motor, a slider, and the like are combined may be adopted. The drive mechanism 14 is not indispensable and the optical fiber 29 may be rotated and slid in the axial direction 101 by handling the proximal end side of the optical fiber 29 by an operator.

The control unit 15 generates laser light with a predetermined light intensity in a predetermined period of time from the laser light generating unit 12, controls the flow amount and the pressure of the fluid returning unit 13, or controls the drive amount and timing of the drive mechanism 14 based on a protocol programmed beforehand, for example. The control unit 15 has an arithmetic unit for performing such operation control.

[Usage Directions for Ablation Device 11]

Hereinafter, the usage directions for the ablation system 10 for cutting a nerve 41 of the renal artery 40 are described.

As illustrated in FIG. 1, the ablation device 11 is connected to the laser light generating unit 12, the fluid returning unit 13, and the drive mechanism 14. The laser light generating unit 12, the fluid returning unit 13, and the drive mechanism 14 are connected to the control unit 15. In the control unit 15, a program suitable for performing the ablation to the renal artery 40 is set beforehand.

The ablation device 11 is inserted into and passed through the renal artery 40 from the distal end side. A guide wire is inserted into and passed through the renal artery 40 beforehand to be caused to reach a target portion while performing imaging under an X-ray fluoroscopy. Such insertion and passing of the guide wire is performed by known techniques disclosed in Japanese Patent Laid-Open Nos. 2006-326226 and 2006-230442, for example.

When the ablation device 11 is inserted into the renal artery 40, a fluid is not injected into the balloon 21, and thus the balloon 21 is in a contraction state. The guide wire is inserted into and passed through the guide wire tube 24 from the distal end of the ablation device 11 in this state. Then, the ablation device 11 is inserted into the renal artery 40 along the guide wire. The insertion position of the ablation device 11 in the renal artery 40 is grasped by, for example, confirming the marker placed in the distal tip 25 under X-rays.

As illustrated in FIG. 3, when the ablation device 11 is inserted into the target portion of the renal artery 40, the fluid returning unit 13 is driven by the control unit 15, so that a fluid is caused to flow into the balloon 21 through the in-side tube 27 from the fluid returning unit 13, and thus the balloon 21 expands. The fluid is returned into the fluid returning unit 13 via the out port 28 through the shaft 22 from the balloon 21. The return of the fluid to the balloon 21 indicated by an arrow 51 in FIG. 3 is controlled in such a manner as to have a desired flow velocity and pressure by controlling the fluid returning unit 13 by the control unit 15. Moreover, the temperature of the fluid stored in the fluid returning unit 13 is controlled to be a temperature suitable for cooling the intima of the renal artery 40.

Subsequently, laser light 42 generated from the laser light generating unit 12 by driving the laser light generating unit 12 and the drive mechanism 14 by the control unit 15 is propagated into the balloon 21 through the optical fiber 29, and then reflected in a direction crossing the axial direction 101 by the reflector 33. The reflected laser light 42 transmits through the in-side tube 27 and the balloon 21 emitted to the vascular wall of the renal artery 40, and then transmits through the vascular wall to reach the nerve 41. Thus, the nerve 41 (indicated by the chain double-dashed line for convenience in FIG. 3) to which the laser light 42 is emitted is subjected to ablation. The intensity and the emission time of the laser light 42 are controlled by the control unit 15.

Moreover, due to the fact that the drive mechanism 14 is driven by the control unit 15, the optical fiber 29 which propagates the laser light 42 is slid while being rotated in the axial direction 101. Since the reflector 33 is also rotated with the rotation of the optical fiber 29, the direction of the laser light 42 to be reflected by the reflector 33 is displaced in the circumferential direction with respect to the axial direction 101 (Arrow 52). Thus, the ablation can be uniformly performed to the nerve 41 present in the circumferential direction of the renal artery 40. Moreover, since the reflector 33 is also slid with the slide of the optical fiber 29, the laser light 42 to be reflected by the reflector 33 is displaced in the axial direction 101 (Arrow 53). Thus, the ablation can be uniformly performed to the nerve 41 present in a direction in which the renal artery 40 extends (which is the same direction as the axial direction 101).

The rotation and slide pattern of the optical fiber 29 can be arbitrarily set by programming in the control unit 15. Therefore, for example, due to the fact that the optical fiber 29 is slid while being rotated, the laser light 42 can be spirally emitted to the nerve 41 of the renal artery 40. By emitting the laser light 42 from the laser light generating unit 12 when the rotation or slide of the optical fiber 29 is suspended, the laser light 42 can be emitted in a spot shape to the nerve 41 of the renal artery 40. More specifically, the timing, the order, and the like for emitting the laser light 42 to the nerve 41 present in the entire circumference of a predetermined range in the direction in which the renal artery 40 extends can be arbitrarily set.

On the other hand, the laser light 42 reflected by the reflector 33 is also emitted to the tissue of the intima side of the renal artery 40 before reaching the nerve 41 of the renal artery 40. The expanded balloon 21 contacts the intima of the renal artery 40 and a fluid is returned into the balloon 21. The heating to the intima side of the renal artery 40 is suppressed by a cooling effect of the fluid. Therefore, it is suitable to set the slide range of the optical fiber 29 in a range where the balloon 21 contacts the intima of the renal artery 40.

[Operational Effects of First Embodiment]

According to the embodiment described above, heat damages to the intima can be suppressed by suppressing the heating to the intima of the renal artery 40 while performing ablation to the nerve 41 of the renal artery 40.

Moreover, the reflector 33 is integrally provided on the distal end side of the optical fiber 29 and the optical fiber 29 is movable and rotatable in the axial direction 101 with respect to the shaft 22, and therefore the ablation device 11 can be realized with a simple configuration. Moreover, the movement and the rotation of the reflector 33 can be operated through the optical fiber 29 on the proximal end side of the shaft 22.

[Modification of First Embodiment]

In this embodiment, although the reflector 33 is integrally provided at the distal end of the optical fiber 29, a member which allows transmission of laser light, such as a lens, may be provided between the distal end of the optical fiber 29 and the reflector 33. Moreover, the distal end of the optical fiber 29 and the reflector 33 may be disposed through space and the optical fiber 29 and the reflector 33 may be connected in such a manner that the movement and the rotation of the optical fiber 29 are transmitted to the reflector 33. Moreover, a configuration may be acceptable in which the optical fiber 29 and the reflector 33 are completely independent and the reflector 33 is fixed to, for example, the in-side tube 27 to be interlocked with the rotation and the movement of the in-side tube 27.

In this embodiment, although the optical fiber 29 is inserted into and passed through the inside of the in-side tube 27, the insertion and passing route of the optical fiber 29 is not limited insofar as the distal end side reaches the inside of the balloon 21. Therefore, the optical fiber 29 may be inserted into and passed through the internal space of the shaft 22 or may be inserted into the balloon 21 from the outside of the shaft 22, for example.

Second Embodiment

Hereinafter, an ablation device 61 according to a second embodiment of the present invention is described. The ablation device 61 configures a part of the ablation system having the laser light generating unit 12, the fluid returning unit 13, the drive mechanisms 14, and the control unit 15 as in the ablation device 11 illustrated in FIG. 1.

As illustrated in FIGS. 4 and 5, the ablation device 61 has a main shaft 72 provided with a balloon 71 on the distal end side thereof. The main shaft 72 is a long member in the axial direction 101. The main shaft 72 is a tubular body which may elastically bend in such a manner as to curve in the axial direction 101. A direction in the state where the main shaft 72 does not curve extends is referred to as the axial direction 101 in this specification.

An in-side tube 77, an optical fiber 79, a sub-shaft 74, and a guide wire shaft 84 are inserted into and passed through the main shaft 72. Although the outer diameter and inner diameter of the main shaft 72 do not necessarily need to be fixed in the axial direction 101, it is preferable that the rigidity on the proximal end side is higher than that on the distal end side from the viewpoint of operability. For the main shaft 72, known materials for use in a balloon catheter, such as synthetic resin and stainless steel, can be used. The main shaft 72 does not necessarily need to be configured from only one material and may be configured by attaching a plurality of parts containing other materials.

In this embodiment, the proximal end refers to the backside (right side in FIG. 4) in a direction in which the ablation device 61 is inserted into a blood vessel. The distal end refers to the front side (left side in FIG. 4) in the direction in which the ablation device 61 is inserted into a blood vessel.

The balloon 71 is provided on the distal end side of the main shaft 72. The balloon 71 elastically expands due to the fact that a fluid (liquid, gas) is caused to flow into the internal space and contracts due to the fact that a fluid is caused to flow out of the internal space. FIG. 4 illustrates the balloon 71 in an expansion state. The internal space of the balloon 71 is communicated with each of the internal space of the shaft 72 and the internal space of the in-side tube 77. When a fluid is caused to flow into the internal space of the balloon 71 through the in-side tube 77, the balloon 71 expands in the radial direction orthogonal to the axial direction 101 in such a manner that the diameter at the center in the axial direction 101 reaches the maximum diameter. Due to the fact that, while a fluid having a flow amount which allows holding of the pressure of the fluid maintaining the expansion of the balloon 71 is being caused to flow into the balloon 71, the fluid is caused to flow out of the balloon 71 through the internal space of the main shaft 72, the fluid is returned into the balloon 71. As the materials of the balloon 71 and a method for fixing the balloon 71 and the main shaft 72, known materials and methods for use in a balloon catheter can be used. The internal space of the in-side tube 77 and the space between the main shaft 72 and the in-side tube 77 are equivalent to the fluid lumen.

With respect to the in-side tube 77 inserted into and passed through the inside of the main shaft 72, the distal end side reaches the internal space of the balloon 71 and the proximal end side is connected to an in port 76 of a connector portion 73. The distal end side of the in-side tube 77 is connected to a distal tip 75 provided on the distal end side of the balloon 71. In the vicinity of the distal tip 75 of the in-side tube 77, openings 80 and 81 penetrating the peripheral wall of the in-side tube 77 are provided. Through the openings 80 and 81, a fluid passing through the internal space of the in-side tube 77 flows out into the balloon 71. The openings 80 and 81 are disposed at positions different in the circumferential direction with respect to the axial direction 101.

The distal tip 75 is provided with a marker containing a contrast media as the raw material. Examples of the contrast medium include barium sulfate, bismuth oxide, and bismuth subcarbonate, for example.

A sub-shaft 74 is inserted into and passed through the in-side tube 77. The sub-shaft 74 is extended from the outside of the connector portion 73 to the inside of the balloon 71. The sub-shaft 74 is a long member in the axial direction 101 and elastically bends in such a manner as to curve in the axial direction 101 and is not connected to the distal tip 75. Therefore, the sub-shaft 74 is a tubular body capable of transmitting the rotation around the axial direction 101 to the distal end side from the connector portion 73 side. The sub-shaft 74 is a tubular body configured from a stainless steel coil, for example.

A guide wire shaft 84 is inserted a sub-shaft 74 is inserted into and passed through the internal space of the sub-shaft 74. The guide wire shaft 84 is connected to the distal tip 75. In the distal tip 75, a hole 85 along the axial direction 101 is formed in such a manner as to cause the internal space of the guide wire shaft 84 to communicate with the outside. The distal end of the guide wire shaft 84 is inserted into and passed through the hole 85 to reach the distal end of the distal tip 75. As the raw materials of the guide wire shaft 84, known materials may be adopted. The internal space of the guide wire shaft 84 is equivalent to the wire lumen.

The optical fiber 79 is extended in the axial direction 101 while being bonded to the outer periphery of the sub-shaft 74 from the outside of the connector portion 73 to reach the inside of the balloon 71. The optical fiber 79 propagates laser light, which is generated by the laser light generating unit 12 and is emitted to the proximal end of the optical fiber 79, to the distal end. For the optical fiber 79, those having a refractive index which allows total reflection in the wavelength of the laser light are adopted as appropriate. Specifically, a single mode fiber, a polarization maintaining fiber, a multimode fiber, and a bundle fiber for image transmission are mentioned. The optical fiber 79 is equivalent to the light guide material.

A distal end surface 82 of the optical fiber 79 is a plane which is inclined in such a manner as to form an angle of 45° with respect to the axial direction 101 and in such a manner that the outer surface faces the sub-shaft 74 side. On the distal end surface 82, a reflector 83 is laminated. For the reflector 83, raw materials which totally reflect the laser light propagating through the optical fiber 79 are adopted. As the materials of the reflector 83, a quartz-based glass and the like are adopted but the materials are not particularly limited.

The optical fiber 79 and the reflector 83 are rotatable around the axial direction 101 integrally with the sub-shaft 74 and are slidable in the axial direction 101. The rotation and the slide of the optical fiber 79 and the reflector 83 are controlled by directly or indirectly operating the proximal end side of the sub-shaft 74 extended from the connector portion 73. Specifically, the optical fiber 79 and the reflector 83 are rotated and slid along the outer periphery of the sub-shaft 74 with the sub-shaft 74 by a driving force given from the drive mechanism 14 to the proximal end side of the sub-shaft 74.

Although not illustrated in each view, a temperature sensor may be provided on the outer wall or the like of the in-side tube 77 in the balloon 71. As the temperature sensor, known temperature sensors, such as a thermocouple, can be used, for example, insofar as the temperature sensors can be placed in the balloon 71. The temperature of the fluid in the balloon 71 can be monitored by guiding a cable extended from the temperature sensor to the outside.

As illustrated in FIG. 5, the connector portion 73 is provided on the proximal end side of the main shaft 72. The connector portion 73 is a portion held by an operator when operating the ablation device 61. The connector portion 73 is provided with an out port 78. The out port 78 is continuous with the space between the main shaft 72 and the in-side tube 77. A fluid to be returned into the balloon 71 flows out of the out port 78 through the space.

The connector portion 73 is provided with an in port 76. The in port 76 is continuous with the space between the in-side tube 77 and the sub-shaft 74. A fluid to be returned into the balloon 71 flows in from the in port 76 through the space. In the connector portion 73, the in port 76 and the out port 78 are separated from each other in a fluid-tight manner with O rings 86 and 87. The in port 76 and the out port 78 are connected to the fluid returning unit 13 illustrated in FIG. 1.

The sub-shaft 74 and the optical fiber 79 are extended from the proximal end side of the connector portion 73 to the outside. The sub-shaft 74 and the optical fiber 79 are movable along the axial direction 101 with respect to the connector portion 73 and are rotatable around the axial direction 101. In the connector portion 73, fluid-tightness is secured with an O ring 88 in a portion around the sub-shaft 74 and the optical fiber 79. The optical fiber 79 is connected to the laser light generating unit 12 illustrated in FIG. 1. The sub-shaft 74 is connected to the drive mechanism 14 illustrated in FIG. 1.

The usage directions for the ablation device 61 described above are the same as the usage directions for the ablation device 11. As an example of the usage directions, the ablation device 61 is used as the ablation system 10 illustrated in FIG. 1.

More specifically, the ablation device 61 is inserted into the renal artery 40 from the distal end side. In this state, a guide wire is inserted into and passed through the renal artery 40 beforehand to be caused to reach the target portion, the guide wire is inserted into and passed through the guide wire shaft 84 of the ablation device 61, and then the main shaft 72 of the ablation device 61 is inserted into the renal artery 40 along the guide wire.

Then, when the ablation device 61 is inserted into the target portion of the renal artery 40, a fluid is returned into the balloon 71, so that the balloon 71 expands. Subsequently, laser light is propagated into the balloon 71 through the optical fiber 79, and then reflected to the outside of the main shaft 72 in a direction crossing the axial direction 101 by the reflector 73. The reflected laser light transmits through the in-side tube 77 and the balloon 71 to be emitted to the vascular wall of the renal artery 40, and then transmits through the vascular wall to reach a nerve. Since the optical fiber 79 moves and rotates along the outer periphery of the sub-shaft 74, the laser light to be reflected to the outside of the main shaft 72 is not blocked by the sub-shaft 74 and the guide wire inserted into and passed through the guide wire shaft 84. Therefore, when laser light is emitted to the renal artery 40, i.e., when ablation is performed, the guide wire does not need to be pulled out from the guide wire shaft 84.

[Operational Effects of Second Embodiment]

According to the second embodiment described above, heat damages to the intima can be suppressed by suppressing the heating to the intima of the renal artery while performing ablation to the nerve of the renal artery as in the first embodiment.

Moreover, the optical fiber 79 is fixed to the outer periphery of the sub-shaft 74 and the reflector 83 reflects laser light to the outside of the main shaft 72 in a direction crossing the axial direction 101, and therefore, the reflected laser light is not blocked by the guide wire shaft 84 inserted into and passed through the inside of the sub-shaft 74 and the guide wire inserted into and passed through the guide wire shaft 84. Thus, ablation can be performed in the state where the guide wire is inserted into and passed through the ablation device 61. Moreover, the guide wire shaft 84 is extended from the distal end to the proximal end of the main shaft 72, and therefore, after the guide wire is removed from the ablation device 61, the guide wire is easily inserted into and passed through the ablation device 61 again.

Moreover, the reflector 83 is integrally provided on the distal end side of the optical fiber 79 and the optical fiber 79 is movable and rotatable in the axial direction 101 with the sub-shaft 72, and therefore the ablation device 61 can be realized with a simple configuration. Moreover, the reflector 83 is movable and rotatable by operating the sub-shaft 72 in the connection portion 73.

[Modification of Second Embodiment]

In the second embodiment, although the reflector 83 is integrally provided at the distal end of the optical fiber 79, a member which allows transmission of laser light, such as a lens, may be provided between the distal end of the optical fiber 29 and the reflector 33. Moreover, the distal end of the optical fiber 79 and the reflector 83 may be disposed through space and the optical fiber 79 and the reflector 83 each may be bonded to the sub-shaft 74 in such a manner that the optical fiber 79 and the reflector 33 move and rotate integrally with the sub-shaft 74.

Moreover, a configuration may be acceptable in which the guide wire shaft 84 is not provided and a guide wire is inserted into and passed through the sub-shaft 74.

Third Embodiment

[Ablation System 110]

As illustrated in FIG. 6, an ablation system 110 has an ablation device 111, a laser light generating unit 112, a fluid returning unit 113, a drive mechanism 114, and a control unit 115.

[Ablation Device 111]

As illustrated in FIGS. 6 and 7, the ablation device 111 has a shaft 122 provided with a balloon 121 on the distal end side thereof. The shaft 122 is a long member in the axial direction 101. The shaft 122 is a tubular body which may elastically bend in such a manner as to curve in the axial direction 101. A direction in which the shaft 122 in the state where the shaft 122 does not curve extends is referred to as the axial direction 101 in this specification. The axial direction 101 is equivalent to the first direction.

An in-side tube 127 and a light guide tube 134 are inserted into and passed through the shaft 122. Although the outer diameter and the inner diameter of the shaft 122 do not necessarily need to be fixed in the axial direction 101, it is preferable that the rigidity on the proximal end side is higher than that on the distal end side from the viewpoint of operability. For the shaft 122, known materials for use in a balloon catheter, such as synthetic resin and stainless steel, can be used. The shaft 22 does not necessarily need to contain only one material and may be configured by attaching a plurality of parts containing other materials.

In this embodiment, the proximal end refers to the backside (right side in FIG. 6) in a direction in which the ablation device 111 is inserted into a blood vessel. The distal end refers to the front side (left side in FIG. 6) in the direction in which the ablation device 111 is inserted into a blood vessel.

On the distal end side of the shaft 122, the balloon 121 is provided. The balloon 121 elastically expands due to the fact that a fluid (liquid, gas) is caused to flow into the internal space and contracts due to the fact that a fluid is caused to flow out of the internal space. FIGS. 6 and 7 illustrate the balloon 121 in a contraction state. The internal space of the balloon 121 is communicated with each of the internal space of the shaft 122 and the internal space of the in-side tube 127. When a fluid is caused to flow into the internal space of the balloon 121 through the in-side tube 127, the balloon 121 expands in the radial direction orthogonal to the axial direction 101 in such a manner that the diameter at the center in the axial direction 101 reaches the maximum diameter. Due to the fact that, while a fluid having a flow amount which allows holding of the pressure of the fluid maintaining the expansion of the balloon 121 is being caused to flow into the balloon 121, the fluid is caused to flow out of the balloon 121 through the internal space of the shaft 122, the fluid is returned into the balloon 121. As the materials of the balloon 121 and a method for fixing the balloon 121 and the shaft 122, known materials and methods for use in a balloon catheter can be used. The internal space of the in-side tube 127 and the internal space of the shaft 122 are equivalent to the fluid lumen.

On the proximal end side of the shaft 122, an out port 128 is provided. The out port 128 is continuous with the internal space of the shaft 122. The fluid to be returned into the balloon 121 flows out of the out port 128 through the internal space of the shaft 122.

On the proximal end side of the shaft 122, a hub 123 is provided. An optical fiber 129 is inserted into and passed through the hub 123. The hub 123 is provided with an in port 126 separately from an insertion and passing port of the optical fiber 129. The in port 126 is continuous with the internal space of the in-side tube 127. The fluid to be returned into the balloon 121 flows in from the in port 126 through the internal space of the in-side tube 127.

On the outside of the shaft 122, a guide wire tube 124 is provided. The guide wire tube 124 is sufficiently shorter than the length in the axial direction 101 of the shaft 122. The guide wire tube 124 does not necessarily need to be provided on the outside of the shaft 122. For example, the guide wire tube 124 may be inserted into and passed through the internal space of the shaft 122 when a monorail type is adopted instead of a rapid exchange type as in this embodiment.

With respect to the in-side tube 127 inserted into and passed through the inside of the shaft 122, the distal end side reaches the internal space of the balloon 121 and the proximal end side is connected to the in port 126. The distal end side of the in-side tube 127 is connected to a distal tip 125 provided on the distal end side of the balloon 121. In the vicinity of the distal tip 125 of the in-side tube 127, openings 130 and 131 penetrating the peripheral wall of the in-side tube 127 are provided. Through the openings 130 and 131, a fluid passing through the internal space of the in-side tube 127 flows out into the balloon 21. The openings 130 and 131 are disposed at positions different in the circumferential direction with respect to the axial direction 101.

The distal tip 125 is provided with a marker containing a contrast media as the raw material. Examples of the contrast medium include barium sulfate, bismuth oxide, and bismuth subcarbonate, for example.

The light guide tube 134 is a tubular body which may elastically bend in such a manner as to curve in the axial direction 101. With respect to the light guide tube 134 inserted into and passed through the inside of the in-side tube 127, the distal end reaches the vicinity of the openings 130 and 131 of the in-side tube 127 and the proximal end is extended to the outside through the hub 123. An opening 135 is formed in the side wall at a position in the vicinity of the distal end of the light guide tube 134 in the internal space of the balloon 121. The internal space of the light guide tube 134 is communicated with the outside through the opening 135.

The optical fiber 129 is inserted into and passed through the inside of the light guide tube 134 from the hub 123 to be extended to the opening 135. The inner diameter of the internal space of the light guide tube 134 is equal to the outer diameter of the optical fiber 129. Therefore, the axis line of the optical fiber 129 and the axis line of the light guide tube 134 are almost in agreement with each other. A distal end surface 132 of the optical fiber 129 is orthogonal to the axis line. The optical fiber 129 propagates laser light, which is generated by the laser light generating unit 112 and is emitted to the proximal end of the optical fiber 129, to the distal end. For the optical fiber 129, those having a refractive index which allows total reflection in the wavelength of the laser light are adopted as appropriate. Specifically, a single mode fiber, a polarization maintaining fiber, a multimode fiber, and a bundle fiber for image transmission are mentioned. The optical fiber 129 is equivalent to the light guide material.

In the internal space of the light guide tube 134, a reflector 133 is disposed facing the distal end surface 132 of the optical fiber 129 in the axial direction 101. A reflective surface 136 facing the distal end surface 132 in the reflector 133 is a plane inclined in such a manner as to form an angle of 45° with respect to the axis line of the optical fiber 129. The distal end surface 132 and the reflective surface 136 are exposed to the outside of the light guide tube 134 through the opening 135 of the light guide tube 134. The reflector 133 is a cylindrical body containing an optical fiber, resin, and the like. The outer diameter thereof is equal to the inner diameter of the internal space of the light guide tube 134. Therefore, the axis line of the reflector 133 and the axis line of the light guide tube 134 are almost in agreement with each other. A metal layer is laminated on the surface including the reflective surface 136 in the reflector 133. The metal layer contains nickel, gold, aluminum, chromium, and the like alone or as a mixture and is formed on the surface of the reflector 133 by plating or sputtering.

The optical fiber 129 and the reflector 133 are rotatable around the axis line (axial direction 101) and are slidable in the axial direction 101 integrally with the light guide tube 134 while maintaining the positional relationship of the distal end surface 132 and the reflective surface 136, i.e., the separation distance and the angle of the reflective surface 136. The rotation and the slide of the optical fiber 129 and the reflector 133 are controlled by directly or indirectly operating the proximal end side of the light guide tube 134 extended from the hub 123. Specifically, the light guide tube 134 is rotated and slid by a driving force given from the drive mechanism 114 to the proximal end side of the light guide tube 134.

Although not illustrated in each view, a temperature sensor may be provided on the outer wall or the like of the in-side tube 127 in the balloon 121. As the temperature sensor, known temperature sensors, such as a thermocouple, can be used, for example, insofar as the temperature sensors can be placed in the balloon 121. The temperature of the fluid in the balloon 121 can be monitored by guiding a cable extended from the temperature sensor to the outside. Moreover, a third lumen may be provided in the shaft 122 and imaging members, such as an endoscope, IVUS, and OCT, may be placed therein.

For the laser light generating unit 112, known laser light generating devices can be used. In the laser light generating unit 112, light of an excitation source is given to a laser medium, and then oscillation is caused by the reflection of an optical resonator, so that laser light is output, for example. The laser light output from the laser light generating unit 112 is preferably a continuous wave and the wavelength of the laser light is preferably in the range of 400 to 2000 nm. In particular, when the wavelength of the laser light is in the range of 800 to 1500 nm (915 nm, 980 nm, 1470 nm), a local temperature increase can be confirmed, and thus the intima of a renal artery can be appropriately warmed. The laser light generating unit 112 is connected to the proximal end of the optical fiber 129. The laser light output from the laser light generating unit 112 is emitted to the proximal end surface of the optical fiber 129.

For the fluid returning unit 113, known devices having a roller pump and a syringe pump can be used. The fluid returning unit 113 is connected to the in port 126 and the out port 128 of the ablation device 111 through a flow passage, such as a tube. The fluid returning unit 113 has a tank storing a fluid and supplies a fluid to the in port 126 at a desired flow amount and pressure from the tank by a driving force of a pump. The fluid flowing out of the out port 128 may be returned into the tank or may be discarded as a waste fluid. Moreover, the fluid returning unit 113 may have a cooling device for cooling the fluid in the tank. The fluid is not particularly limited and is preferably a mixed solution of physiological saline and a contrast medium for the purpose of the ablation of a renal artery.

The drive mechanism 114 gives a driving force which rotates and slides the proximal end side of the light guide tube 134 in the axial direction 101, and a mechanism in which a motor, a slider, and the like are combined may be adopted. The drive mechanism 114 is not indispensable and the light guide tube 134 may be rotated and slid in the axial direction 101 by handling the proximal end side of the light guide tube 134 by an operator.

The control unit 115 generates laser light with a predetermined light intensity in a predetermined period of time from the laser light generating unit 112, controls the flow amount and the pressure of the fluid returning unit 113, or controls the drive amount and timing of the drive mechanism 114 based on a protocol programmed beforehand, for example. The control unit 115 has an arithmetic unit for performing such operation control.

[Usage Directions for Ablation Device 11]

Hereinafter, the usage directions for the ablation system 110 for cutting the nerve 41 of the renal artery 40 are described.

As illustrated in FIG. 6, the ablation device 111 is connected to the laser light generating unit 112, the fluid returning unit 113, and the drive mechanism 114. The laser light generating unit 112, the fluid returning unit 113, and the drive mechanism 114 are connected to the control unit 115. In the control unit 115, a program suitable for performing the ablation to the renal artery 40 is set beforehand.

The ablation device 111 is inserted into the renal artery 40 from the distal end side. A guide wire is inserted into and passed through the renal artery 40 beforehand to be caused to reach a target portion while performing imaging under an X-ray fluoroscopy. Such insertion and passing of the guide wire is performed by known techniques disclosed in Japanese Patent Laid-Open Nos. 2006-326226 and 2006-230442, for example.

When the ablation device 111 is inserted into the renal artery 40, a fluid is not injected into the balloon 121, and thus the balloon 121 is in a contraction state. The guide wire is inserted into and passed through the guide wire tube 124 from the distal end of the ablation device 111 in this state. Then, the ablation device 111 is inserted into the renal artery 40 along the guide wire. The insertion position of the ablation device 111 in the renal artery 40 is grasped by, for example, confirming the marker placed in the distal tip 125 under X-rays.

As illustrated in FIG. 8, when the ablation device 111 is inserted into the target portion of the renal artery 40, the fluid returning unit 113 is driven by the control unit 115, so that a fluid, such as physiological saline, is caused to flow into the balloon 121 through the in-side tube 127 from the fluid returning unit 113, and thus the balloon 121 expands. The fluid is returned into the fluid returning unit 113 via the out port 128 through the shaft 122 from the balloon 121. The return of the fluid to the balloon 21 indicated by an arrow 151 in FIG. 8 is controlled in such a manner as to have a desired flow velocity and pressure by controlling the fluid returning unit 113 by the control unit 115. Moreover, the temperature of the fluid stored in the fluid returning unit 113 is controlled to be a temperature suitable for cooling the intima of the renal artery 40.

Subsequently, laser light 42 generated from the laser light generating unit 112 by driving the laser light generating unit 112 and the drive mechanism 114 by the control unit 115 is propagated into the balloon 121 through the optical fiber 129, and then the emitted laser light 42 is reflected in a direction crossing the axial direction 101 (which is equivalent to a direction orthogonal to the axial direction 101, a second direction) by the reflective surface 136 of the reflector 33 on the distal end surface 132. The reflected laser light 42 transmits through the in-side tube 127 and the balloon 121 to be emitted to the vascular wall of the renal artery 40, and then transmits through the vascular wall to reach the nerve 41. Thus, the nerve 41 (indicated by the chain double-dashed line for convenience in FIG. 8) to which the laser light 42 is emitted is subjected to ablation. The intensity and the emission time of the laser light 42 are controlled by the control unit 115.

Moreover, due to the fact that the drive mechanism 114 is driven by the control unit 115, the light guide tube 134 is slid while being rotated in the axial direction 101. Since the optical fiber 129 and the reflector 33 are also rotated with the rotation and the slide of the light guide tube 134, the direction of the laser light 42 to be reflected by the reflector 133 is displaced in the circumferential direction with respect to the axial direction 101 (Arrow 152). Thus, the ablation can be uniformly performed to the nerve 41 present in the circumferential direction of the renal artery 40. The laser light 42 to be reflected by the reflector 133 is displaced in the axial direction 101 (Arrow 153). Thus, the ablation can be uniformly performed to the nerve 41 present in a direction (the same direction as the axial direction 101.) in which the renal artery 40 extends.

The rotation and slide pattern of the light guide tube 134 can be arbitrarily set by programming in the control unit 115. Therefore, for example, due to the fact that the light guide tube 134 is slid while being rotated, the laser light 42 can be spirally emitted to the nerve 41 of the renal artery 40. By emitting the laser light 42 from the laser light generating unit 112 when the rotation or slide of the optical fiber 129 is suspended, the laser light 42 can be emitted in a spot shape to the nerve 41 of the renal artery 40. More specifically, the timing, the order, and the like for emitting the laser light 42 to the nerve 41 present in the entire circumference of a predetermined range in the direction in which the renal artery 40 extends can be arbitrarily set.

On the other hand, the laser light 42 reflected by the reflector 133 is emitted to a tissue of the intima side of the renal artery 40 before reaching the nerve 41 of the renal artery 40. The expanded balloon 121 contacts the intima of the renal artery 40 and a fluid is returned into the balloon 121. The heating to the intima side of the renal artery 40 is suppressed by a cooling effect of the fluid. Therefore, it is suitable to set the slide range of the optical fiber 129 in a range where the balloon 121 contacts the intima of the renal artery 40. A fluid to be returned into the balloon 121 contacts the reflective surface 136 of the reflector 133 through the opening 135 of the light guide tube 134. Thus, the reflective surface 136 is cooled by the fluid.

[Operational Effects of Third Embodiment]

According to the embodiment described above, heat damages to the intima can be suppressed by suppressing the heating to the intima of the renal artery 40 while performing ablation to the nerve 41 of the renal artery 40.

Moreover, since the reflector 133 is disposed facing the distal end surface 132 of the optical fiber 129, the reflector 133 is hard to be damaged by the laser light 42.

Moreover, since the reflector 133 is disposed in a flow passage of the fluid passing into the balloon 121, the reflector 133 is cooled by the fluid and damages caused by the laser light 42 are further suppressed.

Moreover, due to the fact that the reflector 133 is rotated around the axis line of the shaft 122 while being moved along the axial direction 101 in the balloon 121, the laser light 42 is uniformly emitted to the tissue around the renal artery 40.

Moreover, since the optical fiber 129 and the reflector 133 are disposed in the internal space of the light guide tube 134, the optical fiber 129 and the reflector 133 are movable and rotatable in the state of maintaining the mutual positional relationship.

Moreover, since the light guide tube 134 has the opening 135 which allows an external fluid to contact the reflective surface 136 of the reflector 133, the reflective surface 136 of the reflector 133 is cooled by the fluid.

[Modification of Third Embodiment]

In this embodiment, although other members are not provided between the distal end surface 132 of the optical fiber 129 and the reflective surface 136 of the reflector 133, a member which allows transmission of laser light, such as a lens, may be provided between the distal end surface 132 of the optical fiber 129 and the reflective surface 136 of the reflector 133.

Moreover, in this embodiment, although the light guide tube 134 is inserted into and passed through the inside of the in-side tube 127, the insertion and passing route of the light guide tube 134 is not limited insofar as the distal end side reaches the inside of the balloon 121. Therefore, the light guide tube 134 may be inserted into and passed through the internal space of the shaft 122 or may be inserted into the balloon 121 from the outside of the shaft 122, for example.

Fourth Embodiment

Hereinafter, an ablation device 61 according to a fourth embodiment of the present invention is described. The ablation device 61 configures a part of the ablation system having the laser light generating unit 112, the fluid returning unit 113, the drive mechanisms 114, and the control unit 115 as in the ablation device 111 illustrated in FIG. 6.

As illustrated in FIGS. 9 and 10, the ablation device 161 has a main shaft 172 provided with a balloon 171 on the distal end side thereof. The main shaft 172 is a long member in the axial direction 101. The main shaft 172 is a tubular body which may elastically bend in such a manner as to curve in the axial direction 101. A direction in which the main shaft 172 in the state where the main shaft 172 does not curve extends is referred to as the axial direction 101 in this specification.

an in-side tube 177, a sub-shaft 174, a light guide tube 189, and a guide wire shaft 184 are inserted and passed through the main shaft 172. Although the outer diameter and the inner diameter of the main shaft 172 do not necessarily need to be fixed in the axial direction 101, it is preferable that the rigidity on the proximal end side is higher than that on the distal end side from the viewpoint of operability. For the main shaft 172, known materials for use in a balloon catheter, such as synthetic resin and stainless steel, can be used. The main shaft 172 does not necessarily need to contain only one material and may be configured by attaching a plurality of parts containing other materials.

In this embodiment, the proximal end refers to the backside (right side in FIG. 9(A)) in a direction in which the ablation device 161 is inserted into a blood vessel. The distal end refers to the front side (left side in FIG. 9(A)) in the direction in which the ablation device 161 is inserted into a blood vessel.

On the distal end side of the main shaft 172, the balloon 171 is provided. The balloon 171 elastically expands due to the fact that a fluid (liquid, gas) is caused to flow into the internal space and contracts due to the fact that a fluid is caused to flow out of the internal space. FIG. 9 illustrates the balloon 171 in a contraction state. The internal space of the balloon 171 is communicated with each of the internal space of the main shaft 172 and the internal space of the in-side tube 177. When a fluid is caused to flow into the internal space of the balloon 171 through the in-side tube 177, the balloon 171 expands in the radial direction orthogonal to the axial direction 101 in such a manner that the diameter at the center in the axial direction 101 reaches the maximum diameter. Due to the fact that, while a fluid having a flow amount which allows holding of the pressure of the fluid maintaining the expansion of the balloon 171 is being caused to flow into the balloon 171, the fluid is caused to flow out of the balloon 171 through the internal space of the main shaft 172, the fluid is returned into the balloon 171. As the materials of the balloon 171 and a method for fixing the balloon 171 and the main shaft 172, known materials and methods for use in a balloon catheter can be used. The internal space of the in-side tube 177 and the space between the main shaft 172 and the in-side tube 177 are equivalent to the fluid lumen.

With respect to the in-side tube 177 inserted into and passed through the inside of the main shaft 172, the distal end side reaches the internal space of the balloon 171 and the proximal end side is connected to an in port 176 of a connector portion 173. The distal end side of the in-side tube 177 is connected to a distal tip 125 provided on the distal end side of the balloon 171. In the vicinity of the distal tip 175 of the in-side tube 177, openings 180 and 181 penetrating the peripheral wall of the in-side tube 177 are provided. Through the openings 180 and 181, a fluid passing through the internal space of the in-side tube 177 flows out into the balloon 171. The openings 180 and 181 are disposed at positions different in the circumferential direction with respect to the axial direction 101.

The distal tip 125 is provided with a marker containing a contrast media as the raw material. Examples of the contrast medium include barium sulfate, bismuth oxide, and bismuth subcarbonate, for example.

A sub-shaft 174 is inserted and passed through the in-side tube 177. The sub-shaft 174 is extended from the outside of the connector portion 173 to the inside of the balloon 171.

The sub-shaft 174 is a long member in the axial direction 101 and elastically bends in such a manner as to curve in the axial direction 101 and is not connected to the distal tip 175. Therefore, the sub-shaft 74 is a tubular body capable of transmitting the rotation around the axial direction 101 to the distal end side from the connector portion 173 side. The sub-shaft 174 is a tubular body configured from a stainless steel coil, for example.

The guide wire shaft 184 is inserted and passed through the internal space of the sub-shaft 174. The guide wire shaft 184 is connected to a distal tip 175. In the distal tip 175, a hole 185 along the axial direction 101 is formed in such a manner as to cause the internal space of the guide wire shaft 184 to communicate with the outside. The distal end of the guide wire shaft 184 is inserted into and passed through the hole 185 to reach the distal end of the distal tip 175. As the raw materials of the guide wire shaft 184, known materials may be adopted. The internal space of the guide wire shaft 184 is the wire lumen.

The light guide tube 189 is a tubular body which may elastically bend in such a manner as to curve in the axial direction 101. The light guide tube 189 is extended in the axial direction 101 while being bonded to the outer periphery of the sub-shaft 174 from the outside of the connector portion 173 to reach the inside of the balloon 171. An opening 190 is formed in the side wall at a position in the vicinity of the distal end of the light guide tube 189 in the internal space of the balloon 171. The internal space of the light guide tube 189 is communicated with the outside through the opening 190.

The optical fiber 179 is inserted into and passed through the inside of the light guide tube 189 from the connector portion 173 to be extended to the opening 190. The inner diameter of the internal space of the light guide tube 189 is equal to the outer diameter of the optical fiber 179. Therefore, the axis line of the optical fiber 179 and the axis line of the light guide tube 189 are almost in agreement with each other. A distal end surface 182 of the optical fiber 179 is orthogonal to the axis line. The optical fiber 179 propagates laser light, which is generated by the laser light generating unit 112 and is emitted to the proximal end of the optical fiber 179, to the distal end. For the optical fiber 179, those having a refractive index which allows total reflection in the wavelength of the laser light are adopted as appropriate. Specifically, a single mode fiber, a polarization maintaining fiber, a multimode fiber, and a bundle fiber for image transmission are mentioned. The optical fiber 179 is equivalent to the light guide material.

In the internal space of the light guide tube 189, a reflector 183 is disposed facing the distal end surface 132 of the optical fiber 179 in the axial direction 101. A reflective surface 191 facing the distal end surface 182 in the reflector 183 is a plane inclined in such a manner as to form an angle of 45° with respect to the axis line of the optical fiber 179. The distal end surface 182 and the reflective surface 191 are exposed to the outside of the light guide tube 189 through the opening 190 of the light guide tube 189. The reflector 183 is a cylindrical body containing an optical fiber, resin, and the like. The outer diameter thereof is equal to the inner diameter of the internal space of the light guide tube 189. Therefore, the axis line of the reflector 183 and the axis line of the light guide tube 189 are almost in agreement with each other. In the reflector 183, a metal layer is laminated on the surface including the reflective surface 191. The metal layer contains nickel, gold, aluminum, chromium, and the like alone or as a mixture and is formed on the surface of the reflector 83 by plating or sputtering.

The optical fiber 179 and the reflector 183 are rotatable around the axial direction 101 and are slidable in the axial direction 101 integrally with the sub-shaft 174 and the light guide tube 189 while maintaining the positional relationship of the distal end surface 182 and the reflective surface 191, i.e., the separation distance and the angle of the reflective surface 191. The rotation and the slide of the optical fiber 179 and the reflector 183 are controlled by directly or indirectly operating the proximal end side of the sub-shaft 174 extended from the connector portion 173. Specifically, the sub-shaft 174 is rotated and slid by a driving force given from the drive mechanism 114 to the proximal end side of the sub-shaft 174.

Although not illustrated in each view, a temperature sensor may be provided on the outer wall or the like of the in-side tube 177 in the balloon 171. As the temperature sensor, known temperature sensors, such as a thermocouple, can be used, for example, insofar as the temperature sensors can be placed in the balloon 171. The temperature of the fluid in the balloon 171 can be monitored by guiding a cable extended from the temperature sensor to the outside.

As illustrated in FIG. 10, the connector portion 173 is provided on the proximal end side of the main shaft 172. The connector portion 173 is a portion held by an operator when operating the ablation device 161. The connector portion 173 is provided with an out port 178. The out port 178 is continuous with the space between the main shaft 172 and the in-side tube 177. A fluid to be returned into the balloon 171 flows out of the out port 178 through the space.

The connector portion 173 is provided with an in port 176. The in port 176 is continuous with the space between the in-side tube 177 and the sub-shaft 174. A fluid to be returned into the balloon 171 flows in from the in port 176 through the space. In the connector portion 173, the in port 176 and the out port 178 are separated from each other in a fluid-tight manner with O rings 186 and 187. The in port 176 and the out port 178 are connected to the fluid returning unit 113 illustrated in FIG. 6.

The sub-shaft 174 and the light guide tube 189 are extended from the proximal end side of the connector portion 173 to the outside. The sub-shaft 174 and the light guide tube 189 are movable along the axial direction 101 with respect to the connector portion 173 and are rotatable around the axial direction 101. In the connector portion 73, fluid-tightness is secured with an O ring 188 in a portion around the sub-shaft 174 and the light guide tube 189. The optical fiber 179 inserted into the light guide tube 189 is connected to the laser light generating unit 112 illustrated in FIG. 6. The sub-shaft 174 is connected to the drive mechanism 114 illustrated in FIG. 6.

The usage directions for the ablation device 161 described above are the same as the usage directions for the ablation device 111. As an example of the usage directions, the ablation device 161 is used as the ablation system 110 illustrated in FIG. 6.

More specifically, the ablation device 161 is inserted into the renal artery 40 from the distal end side. In this state, the guide wire is inserted into and passed through the renal artery 40 beforehand to be caused to reach the target portion, the guide wire is inserted into the guide wire shaft 184 of the ablation device 161, and then the main shaft 172 of the ablation device 161 is inserted into and passed through the renal artery 40 along the guide wire.

Then, when the ablation device 161 is inserted into the target portion of the renal artery 40, a fluid is returned into the balloon 171, so that the balloon 171 expands. Subsequently, laser light is propagated into the balloon 171 through the optical fiber 179 to be emitted from the distal end surface 182, and then reflected to the outside of the main shaft 172 in a direction crossing the axial direction 101 by the reflective surface 191 of the reflector 183. The reflected laser light transmits through the in-side tube 177 and the balloon 171 to be emitted to the vascular wall of the renal artery 40, and then transmits through the vascular wall to reach a nerve. Since the light guide tube 189 moves and rotates along the outer periphery of the sub-shaft 174, the laser light to be reflected to the outside of the main shaft 172 is not blocked by the sub-shaft 174 and the guide wire inserted into and passed through the guide wire shaft 184. Therefore, when laser light is emitted to the renal artery 40, i.e., when ablation is performed, the guide wire does not need to be pulled out from the guide wire shaft 184.

[Operational Effects of Fourth Embodiment]

According to the fourth embodiment described above, heat damages to the intima can be suppressed by suppressing the heating to the intima of the renal artery 40 while performing ablation to the nerve 41 of the renal artery 40 as in the third embodiment.

Moreover, since the reflector 183 is disposed facing the distal end surface 182 of the optical fiber 179, the reflector 183 is hard to be damaged by laser light.

Moreover, the light guide tube 189 is fixed to the outer periphery of the sub-shaft 174 and the reflector 183 reflects laser light to the outside of the main shaft 172 in a direction crossing the axial direction 101, and therefore, the reflected laser light is not blocked by the guide wire shaft 184 inserted into and passed through the inside of the sub-shaft 174 and the guide wire inserted into and passed through the guide wire shaft 184. Thus, ablation can be performed in the state where the guide wire is inserted into and passed through the ablation device 161. Moreover, the guide wire shaft 184 is extended from the distal end to the proximal end of the main shaft 172, and therefore, after the guide wire is removed from the ablation device 161, the guide wire is easily inserted into and passed through the ablation device 161 again.

[Modification of Fourth Embodiment]

In the fourth embodiment, although other members are not provided between the distal end surface 182 of the optical fiber 179 and the reflective surface 183 of the reflector 183, a member which allows transmission of laser light, such as a lens, may be provided between the distal end surface 182 of the optical fiber 179 and the reflective surface 191 of the reflector 183.

Moreover, a configuration may be acceptable in which the guide wire shaft 184 is not provided and a guide wire is inserted into and passed through the sub-shaft 174.

Fifth Embodiment

[Ablation System 210]

As illustrated in FIG. 11, an ablation system 210 has an ablation device 211, a laser light generating unit 212, a fluid returning unit 213, a drive mechanism 214, and a control unit 215.

[Ablation Device 211]

As illustrated in FIGS. 11 and 12, the ablation device 211 has a shaft 222 provided with a balloon 221 on the distal end side thereof. The shaft 222 is a long member in the axial direction 101. The shaft 222 is a tubular body which may elastically bend in such a manner as to curve in the axial direction 101. A direction in which the shaft 222 in the state the shaft 222 does not curve extends is referred to as the axial direction 101 in this specification. The axial direction 101 is equivalent to the first direction.

An in-side tube 227 and an optical fiber 229 are inserted into and passed through the shaft 222. Although the outer diameter and the inner diameter of the shaft 222 do not necessarily need to be fixed in the axial direction 101, it is preferable that the rigidity on the proximal end side is higher than that on the distal end side from the viewpoint of operability. For the shaft 222, known materials for use in a balloon catheter, such as synthetic resin and stainless steel, can be used. The shaft 222 does not necessarily need to contain only one material and may be configured by attaching a plurality of parts containing other materials.

In this embodiment, the proximal end refers to the backside (right side in FIG. 11) in a direction in which the ablation device 211 is inserted into a blood vessel. The distal end refers to the front side (left side in FIG. 11) in the direction in which the ablation device 211 is inserted into a blood vessel.

On the distal end side of the shaft 222, the balloon 221 is provided. The balloon 121 elastically expands due to the fact that a fluid (liquid, gas) is caused to flow into the internal space and contracts due to the fact that a fluid is caused to flow out of the internal space. FIGS. 11 and 12 illustrate the balloon 221 in a contraction state. The internal space of the balloon 221 is communicated with each of the internal space of the shaft 222 and the internal space of the in-side tube 227. When a fluid is caused to flow into the internal space of the balloon 221 through the in-side tube 227, the balloon 221 expands in the radial direction orthogonal to the axial direction 101 in such a manner that the diameter at the center in the axial direction 101 reaches the maximum diameter. Due to the fact that, while a fluid having a flow amount which allows holding of the pressure of the fluid maintaining the expansion of the balloon 221 is being caused to flow into the balloon 221, the fluid is caused to flow out of the balloon 221 through the internal space of the shaft 222, the fluid is returned into the balloon 221. As the materials of the balloon 121 and a method for fixing the balloon 221 and the shaft 222, known materials and methods for use in a balloon catheter can be used. The internal space of the in-side tube 227 is equivalent to the first lumen. The internal space of the shaft 222 is equivalent to the second lumen.

On the proximal end side of the shaft 222, an out port 228 is provided. The out port 228 is continuous with the internal space of the shaft 222. A fluid to be returned into the balloon 221 flows out of the out port 228 through the internal space of the shaft 222.

On the proximal end side of the shaft 222, a hub 223 is provided. An optical fiber 229 is inserted and passed through the hub 223. The hub 223 is provided with an in port 226 separately from an insertion and passing hole of the optical fiber 229. The in port 226 is continuous with the internal space of the in-side tube 227. A fluid to be returned into the balloon 221 flows in from the in port 226 through the internal space of the in-side tube 227.

As illustrated in FIG. 12, a guide wire tube 224 is provided on the outside of the shaft 222. The guide wire tube 224 is sufficiently shorter than the length in the axial direction 101 of the shaft 222. The guide wire tube 224 does not necessarily need to be provided on the outside of the shaft 222. For example, the guide wire tube 224 may be inserted into and passed through the internal space of the shaft 222 when a monorail type is adopted instead of a rapid exchange type as in this embodiment.

With respect to the in-side tube 227 inserted into and passed through the inside of the shaft 222, the distal end side reaches the internal space of the balloon 221 and the proximal end side is connected to the in port 226. The distal end side of the in-side tube 227 is connected to a distal tip 225 provided on the distal end side of the balloon 221. In the vicinity of the distal tip 225 of the in-side tube 227, openings 230 and 231 penetrating the peripheral wall of the in-side tube 227 are provided. Through the openings 230 and 231, a fluid passing through the internal space of the in-side tube 227 flows out into the balloon 221. The openings 230 and 231 are disposed at positions different in the circumferential direction with respect to the axial direction 101.

The distal tip 225 is provided with a marker containing a contrast media as the raw material. Examples of the contrast medium include barium sulfate, bismuth oxide, and bismuth subcarbonate, for example.

The optical fiber 229 is inserted into and passed through the inside of the in-side tube 227 from the hub 223 to be extended into the balloon 221. The optical fiber 229 propagates laser light, which is generated by the laser light generating unit 212 and is emitted to the proximal end of the optical fiber 229, to the distal end. For the optical fiber 229, those having a refractive index which allows total reflection in the wavelength of the laser light are adopted as appropriate. Specifically, a single mode fiber, a polarization maintaining fiber, a multimode fiber, and a bundle fiber for image transmission are mentioned. The optical fiber 229 is equivalent to the light guide material.

As illustrated in FIG. 12 and FIG. 13, a diffusion member 233 is provided adjacent to a distal end surface 232 of the optical fiber 229 in the in-side tube 227. The diffusion member 233 is a columnar shaped member and the length in the axial direction 101 is shorter than the length in the axial direction 101 of the balloon 221. The diffusion member 233 allows transmission of laser light emitted from a distal end surface 232 of the optical fiber 229 and also diffuses the laser light in such a manner that the travel direction of the laser light is changed, i.e., from the axial direction 101 to a direction crossing the axial direction 101. A quartz-based glass and the like are adopted as the diffusion member 233, for example, but the materials thereof are not particularly limited. The diffusion member 233 is connected to the optical fiber 229 to be integrated therewith and is rotatable or slidable with the optical fiber 229 in the internal space of the in-side tube 227. The diffusion member 233 may be not only one which changes the travel direction of the laser light by refraction but one which changes the travel direction of the laser light by reflection.

As illustrated in FIG. 12 and FIG. 13, a tubular member 234 is provided in the in-side tube 227 in such a manner as to surround the outside of the diffusion member 233. The tubular member 234 is a cylindrical tube-shaped member in which the distal end side and the proximal end side, i.e., a distal tip 225 side and a hub 223 side, are sealed and covers the distal end surface 232 of the optical fiber 229 and the outside of the diffusion member 233. The length in the axial direction 101 of the tubular member 234 is shorter than the length in the axial direction 101 of the balloon 221. The tubular member 234 is connected to the optical fiber 229 inserted into and passed through the proximal end side to be integrated therewith and is rotatable or slidable with the optical fiber 229 in the internal space of the in-side tube 227. More specifically, the optical fiber 229, the diffusion member 233, and the tubular member 234 are integrally rotatable or slidable in the internal space of the in-side tube 227.

In the tubular member 234, a reflective layer 236 is laminated on the inside of a resin layer 235 which allows transmission of laser light. The resin layer 235 contains synthetic resin, such as polyimide, for example. The reflective layer 236 contains a metal or the like which reflects laser light and, for example, is formed by forming gold plating on the inner surface side of the resin layer 235. The reflective layer 236 is present on the inner surface side facing the diffusion member 233 and the sealed distal end side. The reflective layer 236 does not necessarily need to totally reflect laser light and may partially or entirely absorb laser light.

The tubular member 234 has a transmission window 237 formed in the cylindrical tube-shaped peripheral wall. The transmission window 237 is formed by removing a part of the reflective layer 236. For example, the transmission window 237 is formed by masking the inner surface of the resin layer 235 corresponding to the transmission window 237 when gold plating, which serves as the reflective layer 236, is formed. The transmission window 237 has a long and narrow spiral shape extending along the axial direction 101. In the transmission window 237, laser light can be transmitted to the outside from the internal space side of the tubular member 234.

The optical fiber 229, the diffusion member 233, and the tubular member 234 are rotatable around the axial direction 101 and are slidable in the axial direction 101 integrally with respect to the in-side tube 227. The rotation and the slide of the optical fiber 229, the diffusion member 233, and the tubular member 234 are controlled by directly or indirectly operating the proximal end side of the optical fiber 229 extended from the hub 223. Specifically, the optical fiber 229 is rotated and slid by a driving force given from the drive mechanism 214 to the proximal end side of the optical fiber 229. Thus, the position in the circumferential direction with respect to the axial direction 101 and the position in the axial direction 101 of the transmission window 237 of the tubular member 234 are displaced.

Although not illustrated in each view, a temperature sensor may be provided on the outer wall or the like of the in-side tube 227 in the balloon 221. As the temperature sensor, known temperature sensors, such as a thermocouple, can be used, for example, insofar as the temperature sensors can be placed in the balloon 221. The temperature of the fluid in the balloon 221 can be monitored by guiding a cable extended from the temperature sensor to the outside. Moreover, a third lumen may be provided in the shaft 222 and imaging members, such as an endoscope, IVUS, and OCT, may be placed therein.

For the laser light generating unit 212, known laser light generating devices can be used. In the laser light generating unit 12, light of an excitation source is given to a laser medium, and then oscillation is caused by the reflection of an optical resonator, so that laser light is output, for example. The laser light output from the laser light generating unit 212 is preferably a continuous wave and the wavelength of the laser light is preferably in the range of 400 to 2000 nm. In particular, when the wavelength of the laser light is in the range of 800 to 1500 nm (915 nm, 980 nm, 1470 nm), a local temperature increase can be confirmed, and thus the intima of a renal artery can be appropriately warmed. The laser light generating unit 212 is connected to the proximal end of the optical fiber 29. The laser light output from the laser light generating unit 212 is emitted to the proximal end surface of the optical fiber 229.

For the fluid returning unit 213, known devices having a roller pump and a syringe pump can be used. The fluid returning unit 213 is connected to the in port 226 and the out port 228 of the ablation device 211 through a flow passage, such as a tube. The fluid returning unit 213 has a tank storing a fluid and supplies a fluid to the in port 226 at a desired flow amount and pressure from the tank by a driving force of a pump. The fluid flowing out of the out port 228 may be returned into the tank or may be discarded as a waste fluid. Moreover, the fluid returning unit 213 may have a cooling device for cooling the fluid in the tank. The fluid is not particularly limited and is preferably a mixed solution of physiological saline and a contrast medium for the purpose of the ablation of a renal artery.

The drive mechanism 214 gives a driving force which rotates and slides the proximal end side of the optical fiber 229 in the axial direction 101, and a mechanism in which a motor, a slider, and the like are combined may be adopted. The drive mechanism 214 is not indispensable and the optical fiber 229 may be rotated and slid in the axial direction 101 by handling the proximal end side of the optical fiber 29 by an operator.

The control unit 215 generates laser light with a predetermined light intensity in a predetermined period of time from the laser light generating unit 212, controls the flow amount and the pressure of the fluid returning unit 213, or controls the drive amount and timing of the drive mechanism 214 based on a protocol programmed beforehand, for example. The control unit 215 has an arithmetic unit for performing such operation control.

[Usage Directions for Ablation Device 211]

Hereinafter, the usage directions for the ablation system 210 for cutting a nerve 41 of the renal artery 40 are described.

As illustrated in FIG. 11, the ablation device 211 is connected to the laser light generating unit 212, the fluid returning unit 213, and the drive mechanism 214. The laser light generating unit 212, the fluid returning unit 213, and the drive mechanism 214 are connected to the control unit 215. In the control unit 215, a program suitable for performing the ablation to the renal artery 40 is set beforehand.

The ablation device 211 is inserted into and passed through the renal artery 40 from the distal end side. A guide wire is inserted into the renal artery 40 beforehand to be caused to reach a target portion while performing imaging under an X-ray fluoroscopy. Such insertion and passing of the guide wire is performed by known techniques disclosed in Japanese Patent Laid-Open Nos. 2006-326226 and 2006-230442, for example.

When the ablation device 211 is inserted into the renal artery 40, a fluid is not injected into the balloon 221, and thus the balloon 221 is in a contraction state. The guide wire is inserted into and passed through the guide wire tube 224 from the distal end of the ablation device 211 in this state. Then, the ablation device 211 is inserted into the renal artery 40 along the guide wire. The insertion position of the ablation device 211 in the renal artery 40 is grasped by, for example, confirming the marker placed in the distal tip 225 under X-rays.

As illustrated in FIG. 14, when the ablation device 211 is inserted into the target portion of the renal artery 40, the fluid returning unit 213 is driven by the control unit 215, so that a fluid is caused to flow into the balloon 221 through the in-side tube 227 from the fluid returning unit 213, and thus the balloon 221 expands. The fluid is returned into the fluid returning unit 213 via the out port 228 through the shaft 222 from the balloon 221. The return of the fluid to the balloon 221 is controlled in such a manner as to have a desired flow velocity and pressure by controlling the fluid returning unit 213 by the control unit 215. Moreover, the temperature of the fluid stored in the fluid returning unit 213 is controlled to be a temperature suitable for cooling the intima of the renal artery 40.

Subsequently, laser light 42 generated from the laser light generating unit 212 by driving the laser light generating unit 212 and the drive mechanism 214 by the control unit 215 is transmitted into the balloon 221 through the optical fiber 229, and then diffused by the diffusion member 233 in two or more directions crossing the axial direction 101. The diffused laser light 42 is reflected in the internal space of the tubular member 234 by a reflective layer 236 of the tubular member 234. The laser light 42 reaching the transmission window 237 of the tubular member 234 transmits through the transmission window 237, further transmits through the in-side tube 227 and the balloon 221 to be emitted to the vascular wall of the renal artery 40, and then transmits through the vascular wall to reach the nerve 41. Thus, the laser light 42 is emitted to the nerve 41 in a spiral shape by the transmission window 237 of the tubular member 234, so that the nerve 41 is subjected to ablation. The intensity and the emission time of the laser light 42 are controlled by the control unit 15.

Moreover, due to the fact that the drive mechanism 214 is driven by the control unit 215, the optical fiber 229 which transmits the laser light 42 is slid while being rotated in the axial direction 101. Since the diffusion member 233 and the tubular member 234 are also rotated with the rotation of the optical fiber 229, the direction of the laser light 42 transmitting through the transmission window 237 having a spiral shape is displaced in the circumferential direction with respect to the axial direction 101. Thus, the ablation can be uniformly performed to the nerve 41 present in the circumferential direction of the renal artery 40. Moreover, since the transmission window 237 is also slid with the slide of the optical fiber 229, the laser light 42 transmitting through the transmission window 237 is displaced in the axial direction 101. Thus, the ablation can be uniformly performed to the nerve 41 present in a direction in which the renal artery 40 extends (which is the same direction as the axial direction 101).

The rotation and slide pattern of the optical fiber 229 can be arbitrarily set by programming in the control unit 215. By emitting the laser light 42 from the laser light generating unit 212 when the rotation or slide of the optical fiber 229 is suspended, the laser light 42 can be emitted in a spot shape to the nerve 41 of the renal artery 40. More specifically, the timing, the order, and the like for emitting the laser light 42 to the nerve 41 present in the entire circumference of a predetermined range in the direction in which the renal artery 40 extends can be arbitrarily set.

On the other hand, the laser light 42 transmitting through the transmission window 237 is also emitted to the tissue of the intima side of the renal artery 40 before reaching the nerve 41 of the renal artery 40. The expanded balloon 221 contacts the intima of the renal artery 40 and a fluid is returned into the balloon 221. The heating to the intima side of the renal artery 40 is suppressed by a cooling effect of the fluid. Therefore, it is suitable to set the slide range of the optical fiber 229 in a range where the balloon 221 contacts the intima of the renal artery 40.

[Operational Effects of Fifth Embodiment]

According to the embodiment described above, heat damages to the intima can be suppressed by suppressing the heating to the intima of the renal artery 40 while performing ablation to the nerve 41 of the renal artery 40.

Moreover, since the position of the transmission window 237 is displaced by the rotation and the slide of the tubular member 234, the laser light 42 is uniformly emitted to the nerve 41 of the renal artery 40.

Moreover, since the diffusion member 233 and the tubular member 234 are integrally provided on the distal end side of the optical fiber 229, the optical fiber 229 is movable and rotatable in the axial direction 101 in the shaft 222, and therefore the ablation device 211 can be realized with a simple configuration. Moreover, the movement and the rotation of the diffusion member 233 and the tubular member 234 can be operated through the optical fiber 229 on the proximal end side of the shaft 222.

[Modification of fifth embodiment]

In the embodiment described above, although the transmission window 237 of the tubular member 234 has a spiral shape extending in the axial direction 101, the shape of the transmission window 237 may be changed as appropriate. For example, as illustrated in FIG. 15, two or more of transmission windows 238 having a round shape may be provided at different positions in the axial direction 101. The transmission ranges D1, D2, D3, and D4 of the transmission windows 238 are overlapped with the transmission ranges of the transmission windows 238 adjacent to each other in the axial direction 101. The positions of the transmission windows 238 in the circumferential direction with respect to the axial direction 101 are different from each other.

Due to the fact that the tubular member 234 is rotated and slid also by such a plurality of transmission windows 238, laser light is uniformly emitted to the nerve 41 of the renal artery 40.

Moreover, since the direction of the laser light 42 which transmits through each transmission window 238 and travels varies in the circumferential direction with respect to the axial direction 101, the laser light 42 does not concentrate in a specific direction in the circumferential direction with respect to the axial direction 101. Thus, the heating to the inside of the renal artery 40 can be suppressed.

Moreover, since the transmission ranges D1, D2, D3, and D4 of the transmission windows 238 are partially overlapped in the axial direction 101, a portion to which the laser light 42 is not emitted is hard to arise in the axial direction 101 of the renal artery 40.

In the embodiment and the modification described above, although the diffusion member 233 and the tubular member 234 are integrally provided on the distal end of the optical fiber 229, only the tubular member 234 may be configured to be rotatable and slidable and the operating unit operating the tubular member 234 may be extended to the hub 223. For example, a configuration may be acceptable in which the tubular member 234 and the in-side tube 227 are connected to each other and the tubular member 234 to be interlocked with the rotation and the slide of the in-side tube 227.

Moreover, in the embodiment and the modification described above, although the optical fiber 229 is inserted into and passed through the inside of the in-side tube 227, the insertion and passing route of the optical fiber 229 is not limited insofar as the distal end side reaches the inside of the balloon 221. Therefore, the optical fiber 229 may be inserted into and passed through the internal space of the shaft 222 or may be inserted into the balloon 221 from the outside of the shaft 222, for example.

Moreover, in the embodiment and the modification described above, although the tubular member 234 is rotated and slid, the tubular member 234 may be configured to be only rotatable or only slidable. For example, when the tubular member 234 having the transmission window 237 of a spiral shape is provided in such a manner as to have a length equal to the length in the axial direction 101 of the balloon 221, the laser light 42 is uniformly emitted to the nerve 41 of the renal artery 40 in the range of the balloon 221 when the tubular member 234 is rotated.

Moreover, in the embodiment and the modification described above, although the transmission windows 237 and 238 are configured from the resin layer 235, the transmission window may be configured as a hole penetrating the resin layer 235 and the reflective layer 236.

REFERENCE SIGNS LIST

10, 110 Ablation system
11, 61, 111, 161, 211 Ablation device
12, 112 Laser light generating unit
13, 113 Fluid returning unit
21, 71, 121, 171, 221 Balloon
22, 122, 222 Shaft (Second lumen, Fluid lumen)
27, 77, 127, 177, 227 In-side tubes (First lumen, Fluid lumen)
29, 79, 129, 179, 229 Optical fiber (Light guide material)
33, 83, 133, 183 Reflector
72, 172 Main shaft
73 Connector portion
74 Sub-shaft
84 Guide wire shaft (Wire lumen)
136, 191 Reflective surface
134, 189 Light guide tube
135, 190 Opening
233 Diffusion member
234 Tubular member
236 Reflective Layer
237,238 Transmission window

The invention claimed is:

1. An ablation system that comprises:
an ablation device that has a shaft with a distal end;
an inner tube that extends through the shaft, leaving a passage between the inner tube and the shaft, and has an extended section that extends past the distal end of the shaft and has a proximal section without apertures and an apertured distal section;
an elastically expandable balloon that is mounted to the distal end of the shaft, over the extended portion of the inner tube;
at least two apertures that are on the apertured distal section of the inner tube and enable fluid to flow from within the inner tube into the balloon and from there into the passage between the inner tube and the shaft;
a light guide material that guides laser light into the balloon; and
a reflector that is mounted on a distal end of the light guide material for axial movement through the proximal, unapertured section of the extended portion of the inner tube, but not into the apertured distal section of the extended section of the inner tube, is rotatable around the axis of the inner tube, and reflects laser light that is emitted from the light guide material in a non-axial direction, through the proximal, nonapertured section of the extended portion of the inner tube.

2. The ablation system according to claim 1, wherein the system also comprises a laser light generating unit that emits laser light to the light guide material, that laser light having a continuously and periodically changing waveform.

3. An ablation device comprising:
a main shaft having a fluid lumen through which a fluid passes;
a balloon which is provided on a distal end side of the main shaft and which is expandable by the fluid passing through the fluid lumen;
a sub-shaft which has a wire lumen, which allows insertion and passing of a guide wire, and which is inserted into and passed through an inside of the main shaft to be extended into the balloon;
a light guide material which is provided along the sub-shaft and which guides laser light into the balloon; and
a reflector which reflects laser light emitted from the light guide material in a direction crossing an axial direction in the balloon, wherein
the sub-shaft is movable in the axial direction and is rotatable around the axial direction with respect to the main shaft, and
the light guide material and the reflector are movable and rotatable with the sub-shaft.

4. The ablation device according to claim 3, wherein the reflector is integrally provided on a distal end side of the light guide material.

5. The ablation device according to claim 3, wherein the sub-shaft extends into the fluid lumen.

6. The ablation device according to claim 3, wherein
a connector having a port through which a fluid passes is connected to a proximal end side of the main shaft,
the port is connected to the fluid lumen in such a manner that a fluid can pass, and
the sub-shaft and the light guide material are rotatable around the axial direction with respect to the connector.

7. An ablation system comprising:
the ablation device according to claim 3;
a laser light generating unit emitting laser light to the light guide material; and
a fluid returning unit returning a fluid into an internal space of the balloon through the fluid lumen.

* * * * *

UNITED STATES PATENT AND TRADEMARK OFFICE
CERTIFICATE OF CORRECTION

PATENT NO. : 10,631,930 B1
APPLICATION NO. : 15/028090
DATED : April 28, 2020
INVENTOR(S) : Miyagawa et al.

It is certified that error appears in the above-identified patent and that said Letters Patent is hereby corrected as shown below:

On the Title Page

Item (54), "(54)" should be -- (54) --.

Item (57), in Column 2, under "ABSTRACT", Line 15, "axial direction 191" should be -- axial direction 101 --.

Signed and Sealed this
Thirty-first Day of May, 2022

Katherine Kelly Vidal
*Director of the United States Patent and Trademark Office*